(12) United States Patent
Jackson et al.

(10) Patent No.: US 11,975,200 B2
(45) Date of Patent: May 7, 2024

(54) DIRECTIONAL STIMULATION PROGRAMMING

(71) Applicant: Medtronic, Inc., Minneapolis, MN (US)

(72) Inventors: Jadin C. Jackson, Roseville, MN (US); Rene A. Molina, Maple Grove, MN (US); Christopher L. Pulliam, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 64 days.

(21) Appl. No.: 17/651,500

(22) Filed: Feb. 17, 2022

(65) Prior Publication Data

US 2022/0266033 A1  Aug. 25, 2022

Related U.S. Application Data

(60) Provisional application No. 63/153,313, filed on Feb. 24, 2021.

(51) Int. Cl.
*A61N 1/36* (2006.01)
*A61N 1/05* (2006.01)
*A61N 1/372* (2006.01)

(52) U.S. Cl.
CPC ....... *A61N 1/36192* (2013.01); *A61N 1/0534* (2013.01); *A61N 1/36135* (2013.01);
(Continued)

(58) Field of Classification Search
CPC .............. A61N 1/0534; A61N 1/36067; A61N 1/36132; A61N 1/36135; A61N 1/36139;
(Continued)

(56) References Cited

U.S. PATENT DOCUMENTS 8,868,173 B2  10/2014  Nelson et al.
8,929,991 B2   1/2015  Fowler et al.
(Continued)

FOREIGN PATENT DOCUMENTS

WO  2016144940 A1   9/2016
WO  2017158067 A1   9/2017
WO  2019204884 A1  10/2019

OTHER PUBLICATIONS

Response to Extended Search Report dated Jul. 15, 2022, from counterpart European Application No. 22158607.6 filed Feb. 27, 2023, 2 pp.
(Continued)

*Primary Examiner* — Amanda K Hulbert
(74) *Attorney, Agent, or Firm* — Shumaker & Sieffert, P.A.

(57) ABSTRACT

Devices, systems, and techniques are disclosed for managing electrical stimulation therapy and/or sensing of physiological signals such as brain signals. For example, a system is configured to receive, for each electrode combination of a plurality of electrode combinations, information representing a signal sensed in response to first electrical stimulation delivered to a patient via a lead, wherein the plurality of electrode combinations comprise different electrode combinations comprising electrode disposed at different positions around a perimeter of the lead implanted in the patient. The system may also be configured to determine, based on the information for each electrode combination of the plurality of electrode combinations, values for a threshold at different locations around the perimeter of the lead and determine, based on the values for the threshold, one or more stimulation parameter values that at least partially define second electrical stimulation deliverable to the patient via the lead.

25 Claims, 20 Drawing Sheets

(52) U.S. Cl.
CPC ..... *A61N 1/36164* (2013.01); *A61N 1/36171* (2013.01); *A61N 1/36175* (2013.01); *A61N 1/3727* (2013.01)

(58) Field of Classification Search
CPC ............ A61N 1/36164; A61N 1/36171; A61N 1/36175; A61N 1/36185; A61N 1/36192; A61N 1/3727
See application file for complete search history.

(56) References Cited

U.S. PATENT DOCUMENTS

| | | | |
|---|---|---|---|
| 9,089,705 | B2 | 7/2015 | Zhu |
| 9,974,959 | B2 | 5/2018 | Moffitt et al. |
| 10,905,887 | B2 * | 2/2021 | Zhang ................ A61N 1/36139 |
| 2003/0139781 | A1 | 7/2003 | Bradley et al. |
| 2007/0203537 | A1 | 8/2007 | Goetz et al. |
| 2008/0125833 | A1 | 5/2008 | Bradley et al. |
| 2011/0054565 | A1 | 3/2011 | Wacnik et al. |
| 2012/0191157 | A1 | 7/2012 | Stypulkowski et al. |
| 2012/0226330 | A1 | 9/2012 | Kolen et al. |
| 2012/0303087 | A1 | 11/2012 | Moffitt et al. |
| 2014/0142549 | A1 | 5/2014 | Su et al. |
| 2015/0202447 | A1 | 7/2015 | Afshar et al. |
| 2016/0303376 | A1 | 10/2016 | Dinsmoor et al. |
| 2016/0319355 | A1 | 11/2016 | Charles et al. |
| 2017/0151437 | A1 | 6/2017 | Moffitt |
| 2018/0085572 | A1 | 3/2018 | Stanslaski et al. |
| 2018/0110991 | A1 | 4/2018 | Molnar et al. |
| 2018/0272142 | A1 | 9/2018 | Zhang et al. |
| 2018/0304075 | A1 | 10/2018 | Su et al. |
| 2018/0353759 | A1 | 12/2018 | Starr et al. |
| 2019/0009098 | A1 | 1/2019 | Jiang et al. |
| 2019/0030321 | A1 | 1/2019 | Tinkhauser et al. |
| 2019/0110754 | A1 | 4/2019 | Rao et al. |
| 2019/0134382 | A1 | 5/2019 | Agnesi et al. |
| 2019/0366074 | A1 | 12/2019 | Carlton et al. |
| 2019/0388679 | A1 | 12/2019 | Geva et al. |
| 2020/0038660 | A1 | 2/2020 | Torgerson |
| 2020/0078594 | A1 | 3/2020 | Jiang et al. |

OTHER PUBLICATIONS

Bouthour et al., "Dyskinesia-Inducing Lead Contacts Optimize Outcome of Subthalamic Stimulation in Parkinson's Disease," Movement Disorders, vol. 34, No. 11, Sep. 30, 2019, pp. 1728-1734.

Hooper et al., "Dyskinetic Storm Induced by Intra-Operative Deep Brain Stimulator Placement," The Open Neurosurgery Journal, vol. 2, No. 1, Feb. 2009, 3 pp.

Matzel et al., "Sacral Neuromodulation: Standardized Electrode Placement Technique," Neuromodulation: Technology at the Neural Interface, Oct. 4, 2017, 9 pp.

Moyer et al., "Stimulation-Induced Dyskinesias Inform Basal Ganglia Models and the Mechanisms of Deep Brain Stimulation," The Journal of Neuroscience, vol. 27, No. 8, Feb. 21, 2007, pp. 1799-1800.

Swann et al., "Gamma Oscillations in the Hyperkinetic State Detected with Chronic Human Brain Recordings in Parkinson's Disease," The Journal of Neuroscience, vol. 36, No. 24, Jun. 15, 2016, pp. 6445-6458.

Tinkhauser et al., "Directional Local Field Potentials: A Tool to Optimize Deep Brain Stimulation", Movement Disorders, vol. 33, No. 1, Jan. 2018, pp. 159-164.

Zheng et al., "Stimulation-Induced Dyskinesia in the Early Stage after Subthalamic Deep Brain Stimulation," Stereotactic and Functional Neurosurgery, vol. 88, Nov. 20, 2009, pp. 29-34.

Extended European Search Report from counterpart European Application No. 22158607.6 dated Jul. 15, 2022, 6 pp.

* cited by examiner

DIRECTIONAL STIMULATION PROGRAMMING

This application claims the benefit of U.S. Provisional Patent Application No. 63/153,313, filed Feb. 24, 2021, the entire contents of which is incorporated herein by reference.

TECHNICAL FIELD

This disclosure generally relates to electrical stimulation and recording.

BACKGROUND

Medical devices may be external or implanted, and may be used to deliver electrical stimulation therapy to various tissue sites of a patient to treat a variety of symptoms or conditions such as chronic pain, tremor, Parkinson's disease, other movement disorders, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Hence, electrical stimulation may be used in different therapeutic applications, such as deep brain stimulation (DBS), spinal cord stimulation (SCS), pelvic stimulation, gastric stimulation, or peripheral nerve field stimulation (PNFS).

A clinician may select values for a number of programmable parameters in order to define the electrical stimulation therapy to be delivered by the implantable stimulator to a patient. For example, the clinician may select one or more electrodes for delivery of the stimulation, a polarity of each selected electrode, a voltage or current amplitude, a pulse width, and a pulse frequency as stimulation parameters. A set of parameters, such as a set including electrode combination, electrode polarity, voltage or current amplitude, pulse width and pulse rate, may be referred to as a program in the sense that they define the electrical stimulation therapy to be delivered to the patient.

SUMMARY

In general, the disclosure describes devices, systems, and techniques related to managing electrical stimulation and/or sensing of physiological signals. For example, an implantable medical device (IMD) may be coupled to one or more leads carrying an array of electrodes. The IMD may monitor electrical signals sensed by different electrode combinations to determine a therapeutic window for the different electrode combinations and/or different locations with respect to the electrode array. The IMD may use these different therapeutic windows to determine which electrode combinations to use for stimulation therapy and/or monitor changes to the therapeutic window over time (e.g., at multiple different times over minutes, hours, days, months or years). In response to determining that the therapeutic window changes in magnitude at the stimulation location and/or with respect to different electrode combinations, the IMD may change the electrode combination used for stimulation and/or provide an indication of declining or improving condition for the patient. The change in therapeutic window may be due to physiological changes in tissue of the patient and/or movement of the electrodes with respect to the tissue. The sensed signals may be physiological signals generated by tissues at a particular location or generated directly by other electrodes at a location separate from the lead.

In one example, a system includes processing circuitry configured to: receive, for each electrode combination of a plurality of electrode combinations, information representing a signal sensed in response to first electrical stimulation delivered to a patient via a lead, wherein the plurality of electrode combinations comprises different electrode combinations comprising electrode disposed at different positions around a perimeter of the lead implanted in the patient; determine, based on the information for each electrode combination of the plurality of electrode combinations, values for a threshold at different locations around the perimeter of the lead; and determine, based on the values for the threshold, one or more stimulation parameter values that at least partially define second electrical stimulation deliverable to the patient via the lead.

In another example, a method including: receiving, by processing circuitry and for each electrode combination of a plurality of electrode combinations, information representing a signal sensed in response to first electrical stimulation delivered to a patient via a lead, wherein the plurality of electrode combinations comprise different electrode combinations comprising electrode disposed at different positions around a perimeter of the lead implanted in the patient; determining, by the processing circuitry and based on the information for each electrode combination of the plurality of electrode combinations, values for a threshold at different locations around the perimeter of the lead; and determining, by the processing circuitry and based on the values for the threshold, one or more stimulation parameter values that at least partially define second electrical stimulation deliverable to the patient via the lead.

In another example, a computer-readable storage medium comprising instructions that, when executed, cause processing circuitry to: receive, for each electrode combination of a plurality of electrode combinations, information representing a signal sensed in response to first electrical stimulation delivered to a patient via a lead, wherein the plurality of electrode combinations comprise different electrode combinations comprising electrode disposed at different positions around a perimeter of the lead implanted in the patient; determine, based on the information for each electrode combination of the plurality of electrode combinations, values for a threshold at different locations around the perimeter of the lead; and determine, based on the values for the threshold, one or more stimulation parameter values that at least partially define second electrical stimulation deliverable to the patient via the lead.

The details of one or more examples of the techniques of this disclosure are set forth in the accompanying drawings and the description below. Other features, objects, and advantages of the techniques will be apparent from the description and drawings, and from the claims.

DETAILED DESCRIPTION

Figure 1:
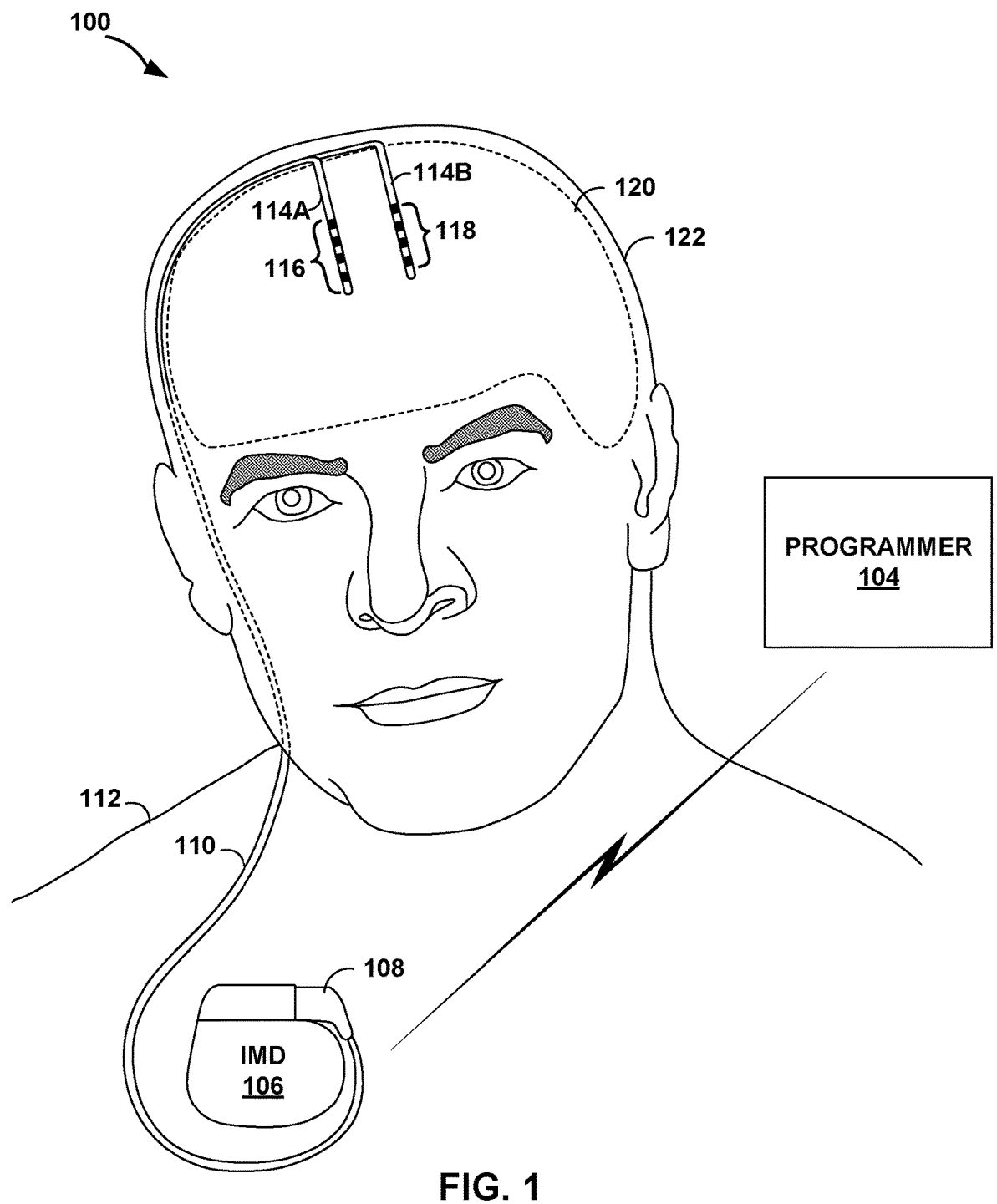
FIG. 1 is a conceptual diagram illustrating an example system that includes an implantable medical device (IMD) configured to deliver DBS to a patient according to an example of the techniques of the disclosure.

This disclosure describes various devices, systems, and techniques for determining that electrodes move with respect to tissue. A patient may suffer from one or more symptoms treatable by electrical stimulation therapy. For example, a patient may suffer from brain disorder such as Parkinson's disease, Alzheimer's disease, or another type of movement disorder. Deep brain stimulation (DBS) may be an effective treatment to reduce the symptoms associated with such disorders. However, efficacy of stimulation therapy may be reliant on selecting appropriate electrodes and other stimulation parameter values that direct an electric field to a target region of tissue. Stimulation of tissue outside of the target region and/or with parameter values too low or too high may elicit undesirable effects and/or reduce the efficacy of the therapy. In addition, a lead, and the electrodes it carries, may move within tissue after implantation. Therefore, if a lead rotates about a longitudinal axis and/or shifts longitudinally within tissue after stimulation parameters are determined, the stimulation therapy may be less effective and/or the stimulation may result in undesirable side effects for the patient. In addition, if the patient's disease progresses or otherwise has physiological changes that occur over time, the prior stimulation parameters may no longer provide effective therapy to treat symptoms or cause new side effects.

As described herein, various devices, systems, and techniques may determine the electrode combinations to use for delivering stimulation therapy, identify electrode movement with respect to tissue, and/or determine disease progression or improvement. A lead may carry a plurality of electrodes at different longitudinal positions and, in some examples, at different positions around the longitudinal axis and the perimeter of the lead. An IMD may be configured to monitor electrical signals (e.g., LFPs) sensed by different electrode combinations over time. For example, the IMD may determine initial information representing electrical signals sensed by different electrode combinations at a first time, such as just after implantation or programming. The system may then determine one or more therapeutic thresholds (e.g., a therapeutic window) associated with the different electrode combinations and select one of the electrode combinations for subsequent stimulation based on the one or more therapeutic thresholds. Each therapeutic threshold may be determined based on signals sensed in response to stimulation of varying intensity (e.g., a sweep of different amplitudes) such as changes in the power of a beta band (low powers indicating reduction in symptoms) or changes in the power of a gamma band (high powers indicating a side effect).

The IMD may periodically (e.g., at regular intervals or in response to a trigger event indicative of a possible lead movement) determine other signal information representing electrical signals sensed by the different electrode combinations at a second time after the first time. For example, the IMD may determine the one or more therapeutic thresholds at different times and identify changes to the one or more therapeutic thresholds. The system may determine that the electrodes have moved with respect to tissue, or that the disease has improving or worsening, based on changes to the one or more therapeutic thresholds over time. In some examples, the IMD may automatically perform a sense electrode survey to obtain updated therapeutic thresholds or prompt a user to perform the sense electrode survey.

Although this disclosure is directed to DBS therapy, the systems, devices, and techniques described herein may similarly detect movement of leads and electrodes implanted outside of the brain, such as near other nerves or muscles for different diagnostic or therapeutic applications, such as spinal cord stimulation (SCS), pelvic stimulation, gastric stimulation, or peripheral nerve field stimulation (PNFS). Moreover, a human patient is described for example purposes herein, but similar systems, devices, and techniques may be used for other animals in other examples.

FIG. 1 is a conceptual diagram illustrating an example system 100 that includes an implantable medical device (IMD) 106 configured to deliver DBS to patient 122 according to an example of the techniques of the disclosure. As shown in the example of FIG. 1, example system 100 includes medical device programmer 104, implantable medical device (IMD) 106, lead extension 110, and leads 114A and 114B with respective sets of electrodes 116, 118. In the example shown in FIG. 1, electrodes 116, 118 of leads 114A, 114B are positioned to deliver electrical stimulation to a tissue site within brain 120, such as a deep brain site under the dura mater of brain 120 of patient 112. In some examples, delivery of stimulation to one or more regions of brain 120, such as the subthalamic nucleus, globus pallidus or thalamus, may be an effective treatment to manage movement disorders, such as Parkinson's disease. Some or all of electrodes 116, 118 also may be positioned to sense neurological brain signals within brain 120 of patient 112. In some examples, some of electrodes 116, 118 may be configured to sense neurological brain signals and others of electrodes 116, 118 may be configured to deliver adaptive electrical stimulation to brain 120. In other examples, all of electrodes 116, 118 are configured to both sense neurological brain signals and deliver adaptive electrical stimulation to brain 120.

IMD 106 includes a therapy module (e.g., which may include processing circuitry, signal generation circuitry or other electrical circuitry configured to perform the functions attributed to IMD 106) that includes a stimulation generator configured to generate and deliver electrical stimulation therapy to patient 112 via a subset of electrodes 116, 118 of leads 114A and 114B, respectively. The subset of electrodes 116, 118 that are used to deliver electrical stimulation to patient 112, and, in some cases, the polarity of the subset of electrodes 116, 118, may be referred to as a stimulation electrode combination. As described in further detail below, the stimulation electrode combination can be selected for a particular patient 112 and target tissue site (e.g., selected based on the patient condition). The group of electrodes 116, 118 includes at least one electrode and can include a plurality of electrodes. In some examples, the plurality of electrodes 116 and/or 118 may have a complex electrode geometry such that two or more electrodes of the lead are located at different positions around the perimeter of the respective lead (e.g., different positions around a longitudinal axis of the lead).

In some examples, the neurological signals (e.g., an example type of electrical signals) sensed within brain 120 may reflect changes in electrical current produced by the sum of electrical potential differences across brain tissue. Examples of neurological brain signals include, but are not limited to, electrical signals generated from local field potentials (LFP) sensed within one or more regions of brain 120, such as an electroencephalogram (EEG) signal, or an electrocorticogram (ECoG) signal. Local field potentials, however, may include a broader genus of electrical signals within brain 120 of patient 112.

In some examples, the neurological brain signals that are used to select a stimulation electrode combination may be sensed within the same region of brain 120 as the target tissue site for the electrical stimulation. As previously indicated, these tissue sites may include tissue sites within anatomical structures such as the thalamus, subthalamic nucleus or globus pallidus of brain 120, as well as other target tissue sites. The specific target tissue sites and/or regions within brain 120 may be selected based on the patient condition. Thus, due to these differences in target locations, in some examples, the electrodes used for delivering electrical stimulation may be different than the electrodes used for sensing neurological brain signals. In other examples, the same electrodes may be used to deliver electrical stimulation and sense brain signals. However, this configuration would require the system to switch between stimulation generation and sensing circuitry and may reduce the time the system can sense brain signals.

Electrical stimulation generated by IMD 106 may be configured to manage a variety of disorders and conditions. In some examples, the stimulation generator of IMD 106 is configured to generate and deliver electrical stimulation pulses to patient 112 via electrodes of a selected stimulation electrode combination. However, in other examples, the stimulation generator of IMD 106 may be configured to generate and deliver a continuous wave signal, e.g., a sine wave or triangle wave. In either case, a stimulation generator within IMD 106 may generate the electrical stimulation therapy for DBS according to a therapy program that is selected at that given time in therapy. In examples in which IMD 106 delivers electrical stimulation in the form of stimulation pulses, a therapy program may include a set of therapy parameter values (e.g., stimulation parameters), such as a stimulation electrode combination for delivering stimulation to patient 112, pulse frequency, pulse width, and a current or voltage amplitude of the pulses. As previously indicated, the electrode combination may indicate the specific electrodes 116, 118 that are selected to deliver stimulation signals to tissue of patient 112 and the respective polarities of the selected electrodes. IMD 106 may deliver electrical stimulation intended to contribute to a therapeutic effect. In some examples, IMD 106 may also, or alternatively, deliver electrical stimulation intended to be sensed by other electrode and/or elicit a physiological response, such as an evoked compound action potential (ECAP), that can be sensed by electrodes.

IMD 106 may be implanted within a subcutaneous pocket above the clavicle, or, alternatively, on or within cranium 122 or at any other suitable site within patient 112. Generally, IMD 106 is constructed of a biocompatible material that resists corrosion and degradation from bodily fluids. IMD 106 may comprise a hermetic housing to substantially enclose components, such as a processor, therapy module, and memory.

Figure 4A:
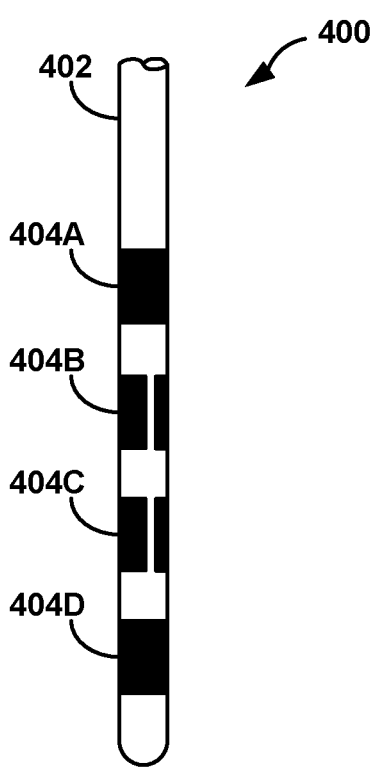
FIGS. 4A and 4B are conceptual diagrams of example leads with respective electrodes carried by the lead.
Figure 4B:
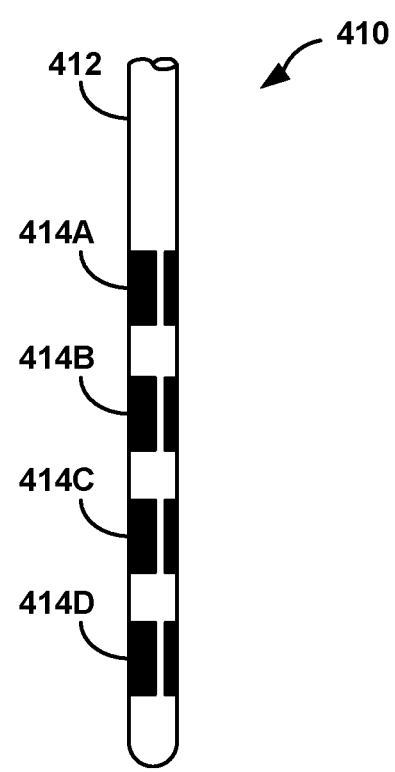

As shown in FIG. 1, implanted lead extension 110 is coupled to IMD 106 via connector 108 (also referred to as a connector block or a header of IMD 106). In the example of FIG. 1, lead extension 110 traverses from the implant site of IMD 106 and along the neck of patient 112 to cranium 122 of patient 112 to access brain 120. In the example shown in FIG. 1, leads 114A and 114B (collectively "leads 114") are implanted within the right and left hemispheres, respectively, of patient 112 in order deliver electrical stimulation to one or more regions of brain 120, which may be selected based on the patient condition or disorder controlled by therapy system 100. The specific target tissue site and the stimulation electrodes used to deliver stimulation to the target tissue site, however, may be selected, e.g., according to the identified patient behaviors and/or other sensed patient parameters. Other lead 114 and IMD 106 implant sites are contemplated. For example, IMD 106 may be implanted on or within cranium 122, in some examples. Or leads 114 may be implanted within the same hemisphere or IMD 106 may be coupled to a single lead implanted in a single hemisphere. Although leads 114 may have ring electrodes at different longitudinal positions as shown in FIG. 1, leads 114 may have electrodes disposed at different positions around the perimeter of the lead (e.g., different circumferential positions for a cylindrical shaped lead) as shown in the examples of FIGS. 4A and 4B.

Leads 114 illustrate an example lead set that include axial leads carrying ring electrodes disposed at different axial positions (or longitudinal positions). In other examples, leads may be referred to as "paddle" leads carrying planar arrays of electrodes on one side of the lead structure. In addition, as described herein, complex lead array geometries may be used in which electrodes are disposed at different respective longitudinal positions and different positions around the perimeter of the lead. As described herein, IMD 106 may be configured to detect movement of the lead with respect to tissue when monitoring electrical signals sensed by the different electrodes between different times.

Although leads 114 are shown in FIG. 1 as being coupled to a common lead extension 110, in other examples, leads 114 may be coupled to IMD 106 via separate lead extensions or directly to connector 108. Leads 114 may be positioned to deliver electrical stimulation to one or more target tissue sites within brain 120 to manage patient symptoms associated with a movement disorder of patient 112. Leads 114 may be implanted to position electrodes 116, 118 at desired locations of brain 120 through respective holes in cranium 122. Leads 114 may be placed at any location within brain 120 such that electrodes 116, 118 are capable of providing electrical stimulation to target tissue sites within brain 120 during treatment. For example, electrodes 116, 118 may be surgically implanted under the dura mater of brain 120 or within the cerebral cortex of brain 120 via a burr hole in cranium 122 of patient 112, and electrically coupled to IMD 106 via one or more leads 114.

In the example shown in FIG. 1, electrodes 116, 118 of leads 114 are shown as ring electrodes. Ring electrodes may be used in DBS applications because they are relatively simple to program and are capable of delivering an electrical field to any tissue adjacent to electrodes 116, 118. In other examples, electrodes 116, 118 may have different configurations. For example, in some examples, at least some of the electrodes 116, 118 of leads 114 may have a complex electrode array geometry that is capable of producing shaped electrical fields. The complex electrode array geometry may include multiple electrodes (e.g., partial ring or segmented electrodes) around the outer perimeter of each lead 114, rather than one ring electrode, such as shown in FIGS. 4A and 4B. In this manner, electrical stimulation may be directed in a specific direction from leads 114 to enhance therapy efficacy and reduce possible adverse side effects from stimulating a large volume of tissue. In some examples, a housing of IMD 106 may include one or more stimulation and/or sensing electrodes. In alternative examples, leads 114 may have shapes other than elongated cylinders as shown in FIG. 1. For example, leads 114 may be paddle leads, spherical leads, bendable leads, or any other type of shape effective in treating patient 112 and/or minimizing invasiveness of leads 114.

In the example shown in FIG. 1, IMD 106 includes a memory to store a plurality of therapy programs that each define a set of therapy parameter values. In some examples, IMD 106 may select a therapy program from the memory based on various parameters, such as sensed patient parameters and the identified patient behaviors. IMD 106 may generate electrical stimulation based on the selected therapy program to manage the patient symptoms associated with a movement disorder.

External programmer 104 wirelessly communicates with IMD 106 as needed to provide or retrieve therapy information. Programmer 104 is an external computing device that the user, e.g., a clinician and/or patient 112, may use to communicate with IMD 106. For example, programmer 104 may be a clinician programmer that the clinician uses to communicate with IMD 106 and program one or more therapy programs for IMD 106. Alternatively, programmer 104 may be a patient programmer that allows patient 112 to select programs and/or view and modify therapy parameters. The clinician programmer may include more programming features than the patient programmer. In other words, more complex or sensitive tasks may only be allowed by the clinician programmer to prevent an untrained patient from making undesirable changes to IMD 106. IMD 106 may also transmit notifications to programmer 104 for delivery to a user in response to detecting that one of leads 114 has moved with respect to tissue. Programmer 104 may enter a new programming session for the user to select new stimulation parameters for subsequent therapy.

When programmer 104 is configured for use by the clinician, programmer 104 may be used to transmit initial programming information to IMD 106. This initial information may include hardware information, such as the type of leads 114 and the electrode arrangement, the position of leads 114 within brain 120, the configuration of electrode array 116, 118, initial programs defining therapy parameter values, and any other information the clinician desires to program into IMD 106. Programmer 104 may also be capable of completing functional tests (e.g., measuring the impedance of electrodes 116, 118 of leads 114). In some examples, programmer 104 may receive sensed signals or representative information and perform the same techniques and functions attributed to IMD 106 herein. In other examples, a remote server (e.g., a standalone server or part of a cloud service) may perform the functions attributed to IMD 106, programmer 104, or any other devices described herein.

The clinician may also store therapy programs within IMD 106 with the aid of programmer 104. During a programming session, the clinician may determine one or more therapy programs that may provide efficacious therapy to patient 112 to address symptoms associated with the patient condition, and, in some cases, specific to one or more different patient states, such as a sleep state, movement state or rest state. For example, the clinician may select one or more stimulation electrode combination with which stimulation is delivered to brain 120. During the programming session, the clinician may evaluate the efficacy of the specific program being evaluated based on feedback provided by patient 112 or based on one or more physiological parameters of patient 112 (e.g., muscle activity, muscle tone, rigidity, tremor, etc.). Alternatively, identified patient behavior from video information may be used as feedback during the initial and subsequent programming sessions. Programmer 104 may assist the clinician in the creation/identification of therapy programs by providing a methodical system for identifying potentially beneficial therapy parameter values.

Programmer 104 may also be configured for use by patient 112. When configured as a patient programmer, programmer 104 may have limited functionality (compared to a clinician programmer) in order to prevent patient 112 from altering critical functions of IMD 106 or applications that may be detrimental to patient 112. In this manner, programmer 104 may only allow patient 112 to adjust values for certain therapy parameters or set an available range of values for a particular therapy parameter.

Programmer 104 may also provide an indication to patient 112 when therapy is being delivered, when patient input has triggered a change in therapy or when the power source within programmer 104 or IMD 106 needs to be replaced or recharged. For example, programmer 112 may include an alert LED, may flash a message to patient 112 via a programmer display, generate an audible sound or somatosensory cue to confirm patient input was received, e.g., to indicate a patient state or to manually modify a therapy parameter.

Therapy system 100 may be implemented to provide chronic stimulation therapy to patient 112 over the course of several months or years. However, system 100 may also be employed on a trial basis to evaluate therapy before committing to full implantation. If implemented temporarily, some components of system 100 may not be implanted within patient 112. For example, patient 112 may be fitted with an external medical device, such as a trial stimulator, rather than IMD 106. The external medical device may be coupled to percutaneous leads or to implanted leads via a percutaneous extension. If the trial stimulator indicates DBS system 100 provides effective treatment to patient 112, the clinician may implant a chronic stimulator within patient 112 for relatively long-term treatment.

Although IMD 106 is described as delivering electrical stimulation therapy to brain 120, IMD 106 may be configured to direct electrical stimulation to other anatomical regions of patient 112 in other examples. In other examples, system 100 may include an implantable drug pump in addition to, or in place of, IMD 106. Further, an IMD may provide other electrical stimulation such as spinal cord stimulation to treat a movement disorder.

According to the techniques of the disclosure, system 100 may, for some or all electrode combinations on leads 116 and 118, determine one or more therapeutic thresholds which alone or in combination may be reflective of a therapeutic window for a patient. Each threshold may correspond to an amplitude of stimulation that at the lower therapeutic threshold begins to suppress symptoms for patient 112 or at an upper therapeutic threshold begins to cause side effects. The therapeutic window correspond to the amplitude range between the upper and lower therapeutic thresholds. In some examples, if a single threshold (e.g., a lower therapeutic threshold or upper therapeutic threshold) is used by system 100, a larger window would correspond to lower amplitudes for the lower therapeutic threshold or higher amplitudes for the upper therapeutic threshold. System 100 may select the electrode combination with the largest therapeutic window.

System 100 can also periodically redetermine the therapeutic window by performing a new electrode sense survey for the different electrodes or electrode combinations. System 100 may determine that the electrodes have moved (e.g., the lead has rotated or moved axially) if the overall therapeutic windows around the lead has stayed generally the same but correspond to different electrodes. Alternatively, system 100 may determine that the disease has changed (e.g., worsened or improved) if the overall therapeutic windows around the lead have changed, such as increased or decreased. In this manner, system 100 can monitor changes to the therapeutic window at different electrodes or electrode combinations over time to identify lead movement and/or physiological changes for the patient.

System 100 (e.g., IMD 106) may also include processing circuitry configured to receive signal information indicative of second electrical signals sensed from the plurality of electrode combinations at a second time after the first time. The processing circuitry or sensing circuitry may generate the signal information based on the sensing circuitry sensing potential differences for each electrode combination. IMD 106 may then determine, based on the signal information, that the lead has rotated with respect to tissue and then output an indication that the lead has rotated with respect to the tissue.

In response to IMD 106 determining that the lead has moved, IMD 106 may perform an action. For example, IMD 106 may control a display to present the indication to a user that the lead has rotated with respect to the tissue. Controlling the display may involve transmitting an alert to external programmer 104 which in turn presents the alert on the display of programmer 104. In some examples, IMD 106 may transmit a request to a user to update stimulation parameter values that define electrical stimulation because the moved lead may no longer provide sufficiency therapy to the patient and/or cause undesirable side effects. In this manner, programmer 104 may receive updated stimulation parameter values (e.g., a different electrode combination to use for stimulation and/or recording) and transmit the updated stimulation parameters back to IMD 106. IMD 106 may then the receive updated stimulation parameters that define electrical stimulation and control stimulation circuitry of IMD 106 to deliver the electrical stimulation according to the updated stimulation parameters. In some examples, IMD 106 or programmer 104 may check whether pre-programmed groups or other parameter sets remain safe or effective with the changed electrode locations in response to determining that the lead has moved. In some examples, IMD 106 and/or programmer 104 can confirm available parameter ranges are safe or appropriate with the moved lead or alert a user when the moved lead is no longer compatible with the new lead position. IMD 106 and/or programmer 104 may inform the user directly or via a cloud-connected platform, for example. Alternatively, IMD 106 and/or programmer 104 may adjust available parameter value ranges in response to the changed electrode locations (e.g., due to the rotation and/or shift).

The architecture of system 100 illustrated in FIG. 1 is shown as an example. The techniques as set forth in this disclosure may be implemented in the example system 100 of FIG. 1, as well as other types of systems not described specifically herein. Nothing in this disclosure should be construed so as to limit the techniques of this disclosure to the example architecture illustrated by FIG. 1.

Figure 2:
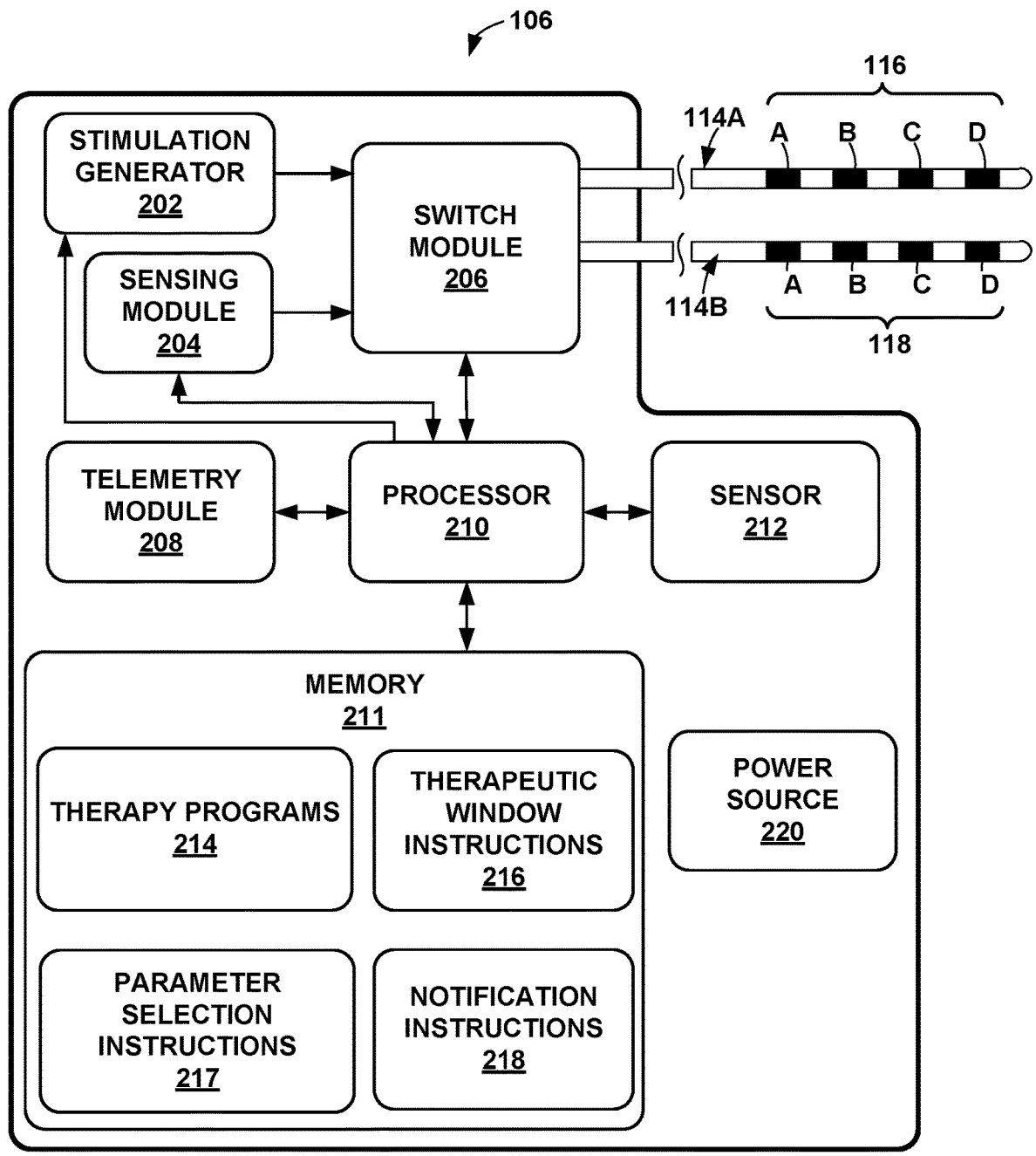
FIG. 2 is a block diagram of the example IMD of FIG. 1 for delivering DBS therapy according to an example of the techniques of the disclosure.

FIG. 2 is a block diagram of the example IMD 106 of FIG. 1 for delivering DBS therapy. In the example shown in FIG. 2, IMD 106 includes processor 210, memory 211, stimulation generator 202, sensing module 204, switch module 206, telemetry module 208, sensor 212, and power source 220. Each of these modules may be or include electrical circuitry configured to perform the functions attributed to each respective module. For example, processor 210 may include processing circuitry, switch module 206 may include switch circuitry, sensing module 204 may include sensing circuitry, and telemetry module 208 may include telemetry circuitry. Switch module 204 may not be necessary for multiple current source and sink configurations. Memory 211 may include any volatile or non-volatile media, such as a random-access memory (RAM), read only memory (ROM), non-volatile RAM (NVRAM), electrically erasable programmable ROM (EEPROM), flash memory, and the like. Memory 211 may store computer-readable instructions that, when executed by processor 210, cause IMD 106 to perform various functions. Memory 211 may be a storage device or other non-transitory medium.

In the example shown in FIG. 2, memory 211 stores therapy programs 214 that include respective stimulation parameter sets that define therapy. Each stored therapy program 214 defines a particular set of electrical stimulation parameters (e.g., a therapy parameter set), such as a stimulation electrode combination, electrode polarity, current or voltage amplitude, pulse width, and pulse rate. In some examples, individual therapy programs may be stored as a therapy group, which defines a set of therapy programs with which stimulation may be generated. The stimulation signals defined by the therapy programs of the therapy group may be delivered together on an overlapping or non-overlapping (e.g., time-interleaved) basis.

Memory 211 may also include therapeutic window instructions 216 that define the process by which processor 210 determines how to determine the one or more therapeutic thresholds for the electrodes. Therapeutic window instructions 216 may also include instructions that define the frequency with which processor 210 controls sensing electrical signals and determining one or more characteristics of the electrical signals that are used to monitor if electrode combinations sensing changes. Memory 211 may also include parameter selection instructions 217 and notification instructions 218. Parameter selection instructions 217 may include instructions that control processor 210 selecting different stimulation parameter values such as electrode combinations, amplitudes, pulse frequencies, or other parameter values for compensating for lead movement. Notification instructions 218 may define instructions that control processor 210 actions such as transmitting an alert or other notification to an external device, such as programmer 104, that indicates the lead has moved with respect to tissue or there is a physiological change. In some examples, notification instructions 218 may also define additional information that processor 210 transmits with the alert, such as an indication of which direction the lead moved, proposed electrode combinations closest to the target tissue after lead movement, or any other information that may assist the user in selecting new stimulation parameters.

In some examples, the sense and stimulation electrode combinations may include the same subset of electrodes 116, 118, a housing of IMD 106 functioning as an electrode, or may include different subsets or combinations of such electrodes. Thus, memory 211 can store a plurality of sense electrode combinations and, for each sense electrode combination, store information identifying the stimulation electrode combination that is associated with the respective sense electrode combination. The associations between sense and stimulation electrode combinations can be determined, e.g., by a clinician or automatically by processor 210. In some examples, corresponding sense and stimulation electrode combinations may comprise some or all of the same electrodes. In other examples, however, some or all of the electrodes in corresponding sense and stimulation electrode combinations may be different. For example, a stimulation electrode combination may include more electrodes than the corresponding sense electrode combination in order to increase the efficacy of the stimulation therapy. In some examples, as discussed above, stimulation may be delivered via a stimulation electrode combination to a tissue site that is different than the tissue site closest to the corresponding sense electrode combination but is within the same region, e.g., the thalamus, of brain 120 in order to mitigate any irregular oscillations or other irregular brain activity within the tissue site associated with the sense electrode combination. In other examples, the electrodes that deliver stimulation may be carried by a lead implanted in a different region of the brain than a different lead that carries the sensing electrodes.

Stimulation generator 202, under the control of processor 210, generates stimulation signals for delivery to patient 112 via selected combinations of electrodes 116, 118. An example range of electrical stimulation parameters believed to be effective in DBS to manage a movement disorder of patient include:

1. Pulse Rate, i.e., Frequency: between approximately 0.1 Hertz and approximately 500 Hertz, such as between approximately 0.1 to 10 Hertz, approximately 40 to 185 Hertz, or such as approximately 140 Hertz.
2. In the case of a voltage controlled system, Voltage Amplitude: between approximately 0.1 volts and approximately 50 volts, such as between approximately 2 volts and approximately 3 volts.
3. In the alternative case of a current controlled system, Current Amplitude: between approximately 0.2 milliamps to approximately 100 milliamps, such as between approximately 1.3 milliamps and approximately 2.0 milliamps.
4. Pulse Width: between approximately 10 microseconds and approximately 5000 microseconds, such as between approximately 100 microseconds and approximately 1000 microseconds, or between approximately 180 microseconds and approximately 450 microseconds.

Accordingly, in some examples, stimulation generator 202 generates electrical stimulation signals in accordance with the electrical stimulation parameters noted above. Other ranges of therapy parameter values may also be useful, and may depend on the target stimulation site within patient 112. While stimulation pulses are described, stimulation signals may be of any form, such as continuous-time signals (e.g., sine waves) or the like. Stimulation signals configured to elicit ECAPs or other evoked physiological signals may be similar or different from the above parameter value ranges.

Processor 210 may include fixed function processing circuitry and/or programmable processing circuitry, and may comprise, for example, any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processor 210 herein may be embodied as firmware, hardware, software or any combination thereof. Processor 210 may control stimulation generator 202 according to therapy programs 214 stored in memory 211 to apply particular stimulation parameter values specified by one or more of programs, such as voltage amplitude or current amplitude, pulse width, or pulse rate.

In the example shown in FIG. 2, the set of electrodes 116 includes electrodes 116A, 116B, 116C, and 116D, and the set of electrodes 118 includes electrodes 118A, 118B, 118C, and 118D. Processor 210 also controls switch module 206 to apply the stimulation signals generated by stimulation generator 202 to selected combinations of electrodes 116, 118. In particular, switch module 204 may couple stimulation signals to selected conductors within leads 114, which, in turn, deliver the stimulation signals across selected electrodes 116, 118. Switch module 206 may be a switch array, switch matrix, multiplexer, or any other type of switching module configured to selectively couple stimulation energy to selected electrodes 116, 118 and to selectively sense neurological brain signals with selected electrodes 116, 118. Hence, stimulation generator 202 is coupled to electrodes 116, 118 via switch module 206 and conductors within leads 114. In some examples, however, IMD 106 does not include switch module 206.

Stimulation generator 202 may be a single channel or multi-channel stimulation generator. In particular, stimulation generator 202 may be capable of delivering a single stimulation pulse, multiple stimulation pulses, or a continuous signal at a given time via a single electrode combination or multiple stimulation pulses at a given time via multiple electrode combinations. In some examples, however, stimulation generator 202 and switch module 206 may be configured to deliver multiple channels on a time-interleaved basis. For example, switch module 206 may serve to time divide the output of stimulation generator 202 across different electrode combinations at different times to deliver multiple programs or channels of stimulation energy to patient 112. Alternatively, stimulation generator 202 may comprise multiple voltage or current sources and sinks that are coupled to respective electrodes to drive the electrodes as cathodes or anodes. In this example, IMD 106 may not require the functionality of switch module 206 for time-interleaved multiplexing of stimulation via different electrodes.

Electrodes 116, 118 on respective leads 114 may be constructed of a variety of different designs. For example, one or both of leads 114 may include two or more electrodes at each longitudinal location along the length of the lead, such as multiple electrodes at different perimeter locations around the perimeter of the lead at each of the locations A, B, C, and D. On one example, the electrodes may be electrically coupled to switch module 206 via respective wires that are straight or coiled within the housing the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 114. These and other constructions may be used to create a lead with a complex electrode geometry.

Although sensing module 204 is incorporated into a common housing with stimulation generator 202 and processor 210 in FIG. 2, in other examples, sensing module 204 may be in a separate housing from IMD 106 and may communicate with processor 210 via wired or wireless communication techniques. Example neurological brain signals include, but are not limited to, a signal generated from local field potentials (LFPs) within one or more regions of brain 28. EEG and ECoG signals are examples of local field potentials that may be measured within brain 120. However, local field potentials may include a broader genus of electrical signals within brain 120 of patient 112. Instead of, or in addition to, LFPs, IMD 106 may be configured to detect patterns of single-unit activity and/or multi-unit activity. IMD 106 may sample this activity at rates above 1,000 Hz, and in some examples within a frequency range of 6,000 Hz to 40,000 Hz. IMD 106 may identify the wave-shape of single units and/or an envelope of unit modulation that may be features used to differentiate or rank electrodes. In some examples, this technique may include phase-amplitude coupling to the envelope or to specific frequency bands in the LFPs sensed from the same or different electrodes.

Sensor 212 may include one or more sensing elements that sense values of a respective patient parameter. For example, sensor 212 may include one or more accelerometers, optical sensors, chemical sensors, temperature sensors, pressure sensors, or any other types of sensors. Sensor 212 may output patient parameter values that may be used as feedback to control delivery of therapy. IMD 106 may include additional sensors within the housing of IMD 106 and/or coupled via one of leads 114 or other leads. In addition, IMD 106 may receive sensor signals wirelessly from remote sensors via telemetry module 208, for example. In some examples, one or more of these remote sensors may be external to patient (e.g., carried on the external surface of the skin, attached to clothing, or otherwise positioned external to the patient). For example, IMD 106 may determine from these one or more additional sensors the brain state of the patient and sense signals for determining electrode movement during a brain state of lower fluctuation or lower noise to improve signal detection. In other examples, IMD 106 may employ an inertial sensor to determine when the patient is at rest (e.g., lying down and/or sleeping) and sense signals for determining lead movement during a time of rest to reduce noise or other motion artifacts in the sensed signals. In some examples, IMD 106 may sense signals for determining lead movement in response to receiving an indication that the patient received a dose of medication or the patient has entered a physician appointment.

Telemetry module 208 supports wireless communication between IMD 106 and an external programmer 104 or another computing device under the control of processor 210. Processor 210 of IMD 106 may receive, as updates to programs, values for various stimulation parameters such as magnitude and electrode combination, from programmer 104 via telemetry module 208. The updates to the therapy programs may be stored within therapy programs 214 portion of memory 211. In addition, processor 210 may control telemetry module 208 to transmit alerts or other information to programmer 104 that indicate a lead moved with respect to tissue. Telemetry module 208 in IMD 106, as well as telemetry modules in other devices and systems described herein, such as programmer 104, may accomplish communication by radiofrequency (RF) communication techniques. In addition, telemetry module 208 may communicate with external medical device programmer 104 via proximal inductive interaction of IMD 106 with programmer 104. Accordingly, telemetry module 208 may send information to external programmer 104 on a continuous basis, at periodic intervals, or upon request from IMD 106 or programmer 104.

Power source 220 delivers operating power to various components of IMD 106. Power source 220 may include a small rechargeable or non-rechargeable battery and a power generation circuit to produce the operating power. Recharging may be accomplished through proximal inductive interaction between an external charger and an inductive charging coil within IMD 220. In some examples, power requirements may be small enough to allow IMD 220 to utilize patient motion and implement a kinetic energy-scavenging device to trickle charge a rechargeable battery. In other examples, traditional batteries may be used for a limited period of time.

According to the techniques of the disclosure, processor 210 of IMD 106 delivers, electrodes 116, 118 interposed along leads 114 (and optionally switch module 206), electrical stimulation therapy to patient 112. The DBS therapy is defined by one or more therapy programs 214 having one or more parameters stored within memory 211. For example, the one or more parameters include a current amplitude (for a current-controlled system) or a voltage amplitude (for a voltage-controlled system), a pulse rate or frequency, and a pulse width, or quantity of pulses per cycle. In examples where the electrical stimulation is delivered according to a "burst" of pulses, or a series of electrical pulses defined by an "on-time" and an "off-time," the one or more parameters may further define one or more of a number of pulses per burst, an on-time, and an off-time.

When a lead rotates or shifts longitudinally, a different electrode combination may be best positioned to stimulate the tissue generating the neurological signal indicative of patient symptoms or of patient side-effects. Therefore, as described herein, processor 210 determines when this shift occurs with the electrodes and determines that the lead has moved. Processor 210 may automatically adjust the electrode combination for delivering therapy and/or other stimulation parameter values to compensate for the moved lead.

Alternatively, processor 210 may transmit an alert to programmer 104 or other external device to indicate that updated stimulation parameters may be needed to continue efficacious therapy. For example, if the adjustments to electrode combinations and/or stimulation parameter values to compensate for the moved lead fall within respective ranges approved by the clinician, processor 210 may automatically adjust the electrode combination and/or other stimulation parameter values. If the adjustments to electrode combinations and/or stimulation parameter values to compensate for the moved lead do not fall within respective ranges approved by the clinician, processor 210 may communicate with programmer 104 to request approval or parameter values from a user.

Figure 3:
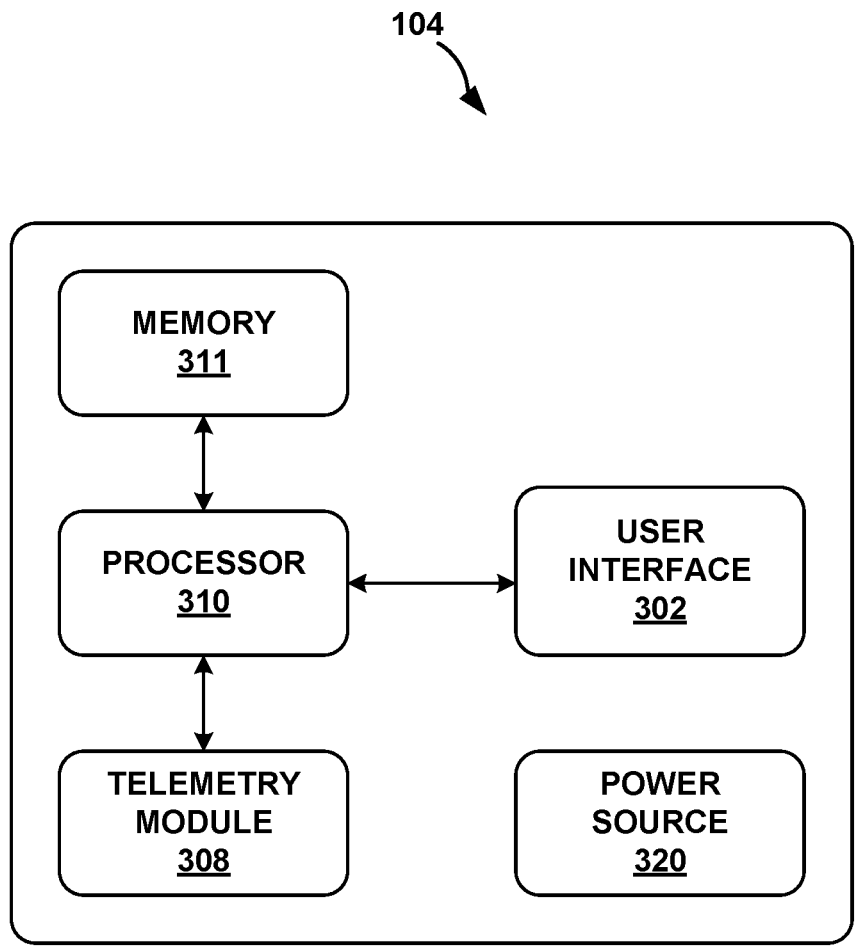
FIG. 3 is a block diagram of the external programmer of FIG. 1 for controlling delivery of DBS therapy according to an example of the techniques of the disclosure.

FIG. 3 is a block diagram of the external programmer 104 of FIG. 1 for controlling delivery of DBS therapy according to an example of the techniques of the disclosure. Although programmer 104 may generally be described as a hand-held device, programmer 104 may be a larger portable device or a more stationary device. In some examples, programmer 104 may be referred to as a tablet computing device. In addition, in other examples, programmer 104 may be included as part of a bed-side monitor, an external charging device or include the functionality of an external charging device. As illustrated in FIG. 3, programmer 104 may include a processor 310, memory 311, user interface 302, telemetry module 308, and power source 320. Memory 311 may store instructions that, when executed by processor 310, cause processor 310 and external programmer 104 to provide the functionality ascribed to external programmer 104 throughout this disclosure. Each of these components, or modules, may include electrical circuitry that is configured to perform some or all of the functionality described herein. For example, processor 310 may include processing circuitry configured to perform the processes discussed with respect to processor 310.

In general, programmer 104 comprises any suitable arrangement of hardware, alone or in combination with software and/or firmware, to perform the techniques attributed to programmer 104, and processor 310, user interface 302, and telemetry module 308 of programmer 104. In various examples, programmer 104 may include one or more processors, which may include fixed function processing circuitry and/or programmable processing circuitry, as formed by, for example, one or more microprocessors, DSPs, ASICs, FPGAs, or any other equivalent integrated or discrete logic circuitry, as well as any combinations of such components. Programmer 104 also, in various examples, may include a memory 311, such as RAM, ROM, PROM, EPROM, EEPROM, flash memory, a hard disk, a CD-ROM, comprising executable instructions for causing the one or more processors to perform the actions attributed to them. Moreover, although processor 310 and telemetry module 308 are described as separate modules, in some examples, processor 310 and telemetry module 308 may be functionally integrated with one another. In some examples, processor 310 and telemetry module 308 correspond to individual hardware units, such as ASICs, DSPs, FPGAs, or other hardware units.

Memory 311 (e.g., a storage device) may store instructions that, when executed by processor 310, cause processor 310 and programmer 104 to provide the functionality ascribed to programmer 104 throughout this disclosure. For example, memory 311 may include instructions that cause processor 310 to obtain a parameter set from memory, select a spatial electrode movement pattern, provide an interface that recommends or otherwise facilitates parameter value selection, or receive a user input and send a corresponding command to IMD 106, or instructions for any other functionality. In addition, memory 311 may include a plurality of programs, where each program includes a parameter set that defines stimulation therapy.

User interface 302 may include a button or keypad, lights, a speaker for voice commands, a display, such as a liquid crystal (LCD), light-emitting diode (LED), or organic light-emitting diode (OLED). In some examples the display may be a touch screen. User interface 302 may be configured to display any information related to the delivery of stimulation therapy, identified patient behaviors, sensed patient parameter values, patient behavior criteria, or any other such information. User interface 302 may also receive user input via user interface 302. The input may be, for example, in the form of pressing a button on a keypad or selecting an icon from a touch screen.

Telemetry module 308 may support wireless communication between IMD 106 and programmer 104 under the control of processor 310. Telemetry module 308 may also be configured to communicate with another computing device via wireless communication techniques, or direct communication through a wired connection. In some examples, telemetry module 308 provides wireless communication via an RF or proximal inductive medium. In some examples, telemetry module 308 includes an antenna, which may take on a variety of forms, such as an internal or external antenna. In some examples, IMD 106 and/or programmer 104 may communicate with remote servers via one or more cloud-services in order to deliver and/or receive information between a clinic and/or programmer.

Examples of local wireless communication techniques that may be employed to facilitate communication between programmer 104 and IMD 106 include RF communication according to the 802.11 or Bluetooth specification sets or other standard or proprietary telemetry protocols. In this manner, other external devices may be capable of communicating with programmer 104 without needing to establish a secure wireless connection. As described herein, telemetry module 308 may be configured to transmit a spatial electrode movement pattern or other stimulation parameter values to IMD 106 for delivery of stimulation therapy.

According to the techniques of the disclosure, in some examples, processor 310 of external programmer 104 defines the parameters of a homeostatic therapeutic window, stored in memory 311, for delivering DBS to patient 112. In one example, processor 311 of external programmer 104, via telemetry module 308, issues commands to IMD 106 causing IMD 106 to deliver electrical stimulation therapy via electrodes 116, 118 via leads 114.

FIGS. 4A and 4B are conceptual diagrams of example leads 400 and 410, respectively, with respective electrodes carried by the lead. As shown in FIGS. 4A and 4B, leads 400 and 410 are embodiments of leads 114 shown in FIG. 1. As shown in FIG. 2A, lead 400 includes four electrode levels 404 (includes levels 404A-404D) mounted at various lengths of lead housing 402. Lead 400 is inserted into through cranium 122 to a target position within brain 18.

Lead 400 is implanted within brain 120 at a location determined by the clinician to be near an anatomical region to be stimulated. Electrode levels 404A, 404B, 404C, and 404D are equally spaced along the axial length of lead housing 30 at different axial positions. Each electrode level 404 may have one, two, three, or more electrodes located at different angular positions around the circumference (e.g., around the perimeter) of lead housing 402. As shown in FIG. 4A, electrode level 404A and 404D include a single respective ring electrode, and electrode levels 404B and 404C each include three electrodes at different circumferential positions. This electrode pattern may be referred to as a 1-3-3-1 lead in reference to the number of electrodes from the proximal end to the distal end of lead 400. Electrodes of one circumferential location may be lined up on an axis parallel to the longitudinal axis of lead 400. Alternatively, electrodes of different electrode levels may be staggered around the circumference of lead housing 402. In addition, lead 400 or 410 may include asymmetrical electrode locations around the circumference, or perimeter, of each lead or electrodes of the same level that have different sizes. These electrodes may include semi-circular electrodes that may or may not be circumferentially aligned between electrode levels.

Lead housing 402 may include a radiopaque stripe (not shown) along the outside of the lead housing. The radiopaque stripe corresponds to a certain circumferential location that allows lead 400 to the imaged when implanted in patient 112. Using the images of patient 112, the clinician can use the radiopaque stripe as a marker for the exact orientation of lead 400 within the brain of patient 112. Orientation of lead 400 may be needed to easily program the stimulation parameters by generating the correct electrode configuration to match the stimulation field defined by the clinician. In other embodiments, a marking mechanism other than a radiopaque stripe may be used to identify the orientation of lead 400. These marking mechanisms may include something similar to a tab, detent, or other structure on the outside of lead housing 402. In some embodiments, the clinician may note the position of markings along a lead wire during implantation to determine the orientation of lead 400 within patient 112. In some examples, programmer 104 may update the orientation of lead 400 in visualizations based on the movement of lead 400 from sensed signals.

FIG. 4B illustrates lead 410 that includes multiple electrodes at different respective circumferential positions at each of levels 414A-414D. Similar to lead 400, lead 410 is inserted through a burr hole in cranium 122 to a target location within brain 120. Lead 410 includes lead housing 412. Four electrode levels 414 (414A-414D) are located at the distal end of lead 410. Each electrode level 414 is evenly spaced from the adjacent electrode level and includes two or more electrodes. In one embodiment, each electrode level 414 includes three, four, or more electrodes distributed around the circumference of lead housing 412. Therefore, lead 410 includes 414 electrodes in a preferred embodiment. Each electrode may be substantially rectangular in shape. Alternatively, the individual electrodes may have alternative shapes, e.g., circular, oval, triangular, rounded rectangles, or the like.

In alternative embodiments, electrode levels 404 or 414 are not evenly spaced along the longitudinal axis of the respective leads 400 and 410. For example, electrode levels 404C and 404D may be spaced approximately 3 millimeters (mm) apart while electrodes 404A and 404B are 10 mm apart. Variable spaced electrode levels may be useful in reaching target anatomical regions deep within brain 120 while avoiding potentially undesirable anatomical regions. Further, the electrodes in adjacent levels need not be aligned in the direction as the longitudinal axis of the lead, and instead may be oriented diagonally with respect to the longitudinal axis.

Leads 400 and 410 are substantially rigid to prevent the implanted lead from varying from the expected lead shape. Leads 400 or 410 may be substantially cylindrical in shape. In other embodiments, leads 400 or 410 may be shaped differently than a cylinder. For example, the leads may include one or more curves to reach target anatomical regions of brain 18. In some embodiments, leads 400 or 410 may be similar to a flat paddle lead or a conformable lead shaped for patient 12. Also, in other embodiments, leads 400 and 410 may any of a variety of different polygonal cross sections (e.g., triangle, square, rectangle, octagonal, etc.) taken transverse to the longitudinal axis of the lead.

As shown in the example of lead 400, the plurality of electrodes of lead 400 includes a first set of three electrodes disposed at different respective positions around the longitudinal axis of the lead and at a first longitudinal position along the lead (e.g., electrode level 404B), a second set of three electrodes disposed at a second longitudinal position along the lead different than the first longitudinal position (e.g., electrode level 404C), and at least one ring electrode disposed at a third longitudinal position along the lead different than the first longitudinal position and the second longitudinal position (e.g., electrode level 404A and/or electrode level 404D). In some examples, electrode level 404D may be a bullet tip or cone shaped electrode that covers the distal end of lead 402.

Figure 5A:
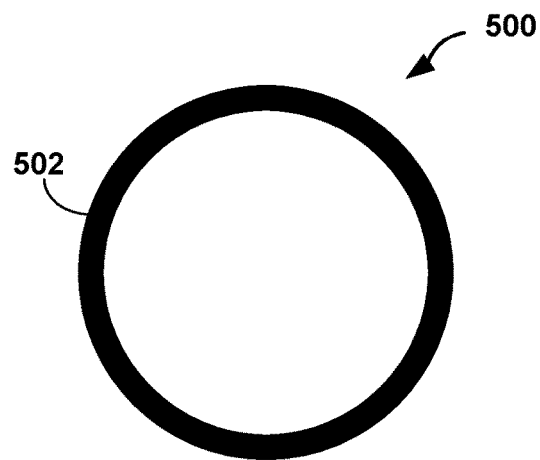
FIGS. 5A, 5B, 5C, and 5D are conceptual diagrams of example electrodes disposed around a perimeter of a lead at a particular longitudinal location.

FIGS. 5A-5D are transverse cross-sections of example stimulation leads having one or more electrodes around the circumference of the lead. As shown in FIGS. 5A-5D, one electrode level, such as one of electrode levels 404 and 414 of leads 400 and 410, are illustrated to show electrode placement around the perimeter, or around the longitudinal axis, of the lead. FIG. 5A shows electrode level 500 that includes circumferential electrode 502. Circumferential electrode 502 encircles the entire circumference of electrode level 500 and may be referred to as a ring electrode in some examples. Circumferential electrode 502 may be utilized as a cathode or anode as configured by the user interface.

Figure 5B:
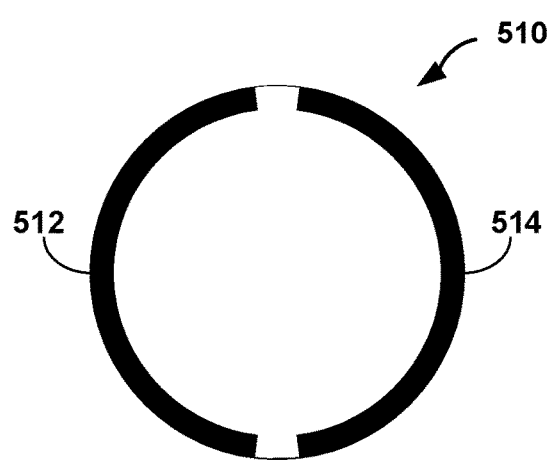

FIG. 5B shows electrode level 510 which includes two electrodes 512 and 514. Each electrode 512 and 514 wraps approximately 170 degrees around the circumference of electrode level 510. Spaces of approximately 10 degrees are located between electrodes 512 and 514 to prevent inadvertent coupling of electrical current between the electrodes. Smaller or larger spaces between electrodes (e.g., between 10 degrees and 30 degrees) may be provided in other examples. Each electrode 512 and 514 may be programmed to act as an anode or cathode.

Figure 5C:
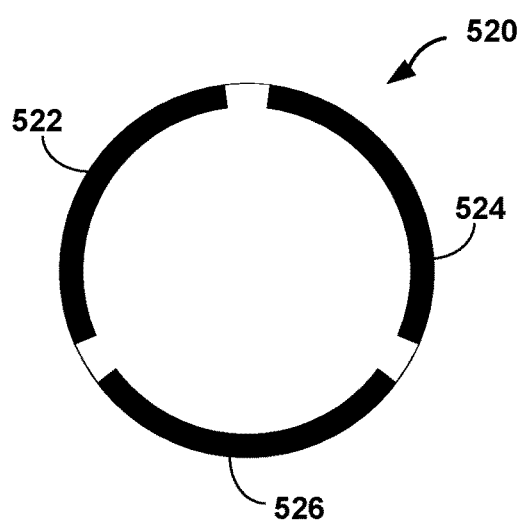

FIG. 5C shows electrode level 520 which includes three equally sized electrodes 522, 524 and 526. Each electrode 522, 524 and 526 encompass approximately 110 degrees of the circumference of electrode level 520. Similar to electrode level 510, spaces of approximately 10 degrees separate electrodes 522, 524 and 526. Smaller or larger spaces between electrodes (e.g., between 10 degrees and 30 degrees) may be provided in other examples. Electrodes 522, 524 and 526 may be independently programmed as an anode or cathode for stimulation.

Figure 5D:
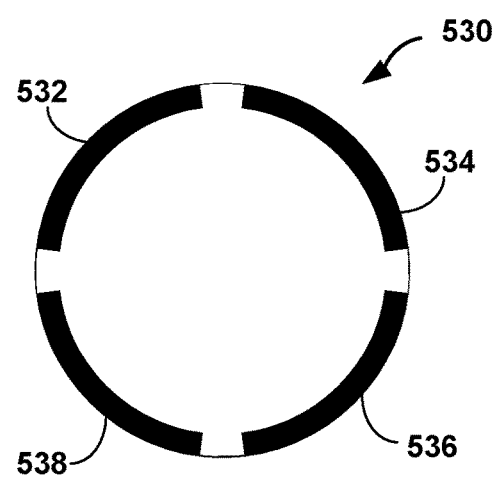

FIG. 5D shows electrode level 530 which includes four electrodes 532, 534, 536 and 538. Each electrode 532, 534, 536 and 538 covers approximately 80 degrees of the circumference with approximately 10 degrees of insulation space between adjacent electrodes. Smaller or larger spaces between electrodes (e.g., between 10 degrees and 30 degrees) may be provided in other examples. In other embodiments, up to ten or more electrodes may be included within an electrode level. In alternative embodiments, consecutive electrode levels of lead 114 may include a variety of electrode levels 500, 510, 520, and 530. For example, lead 114 (or any other lead described herein) may include electrode levels that alternate between electrode levels 510 and 530 depicted in FIGS. 5B and 5D. In this manner, various stimulation field shapes may be produced within brain 120 of patient 112. Further the above-described sizes of electrodes within an electrode level are merely examples, and the invention is not limited to the example electrode sizes.

Also, the insulation space, or non-electrode surface area, may be of any size. Generally, the insulation space is between approximately 1 degree and approximately 20 degrees. More specifically, the insulation space may be between approximately 5 and approximately 15 degrees. In other examples, insulation space may be between approximately 10 degrees and 30 degrees or larger. Smaller insulation spaces may allow a greater volume of tissue to be stimulated. In alternative embodiments, electrode size may be varied around the circumference of an electrode level. In addition, insulation spaces may vary in size as well. Such asymmetrical electrode levels may be used in leads implanted at tissues needing certain shaped stimulation fields.

Figure 6:
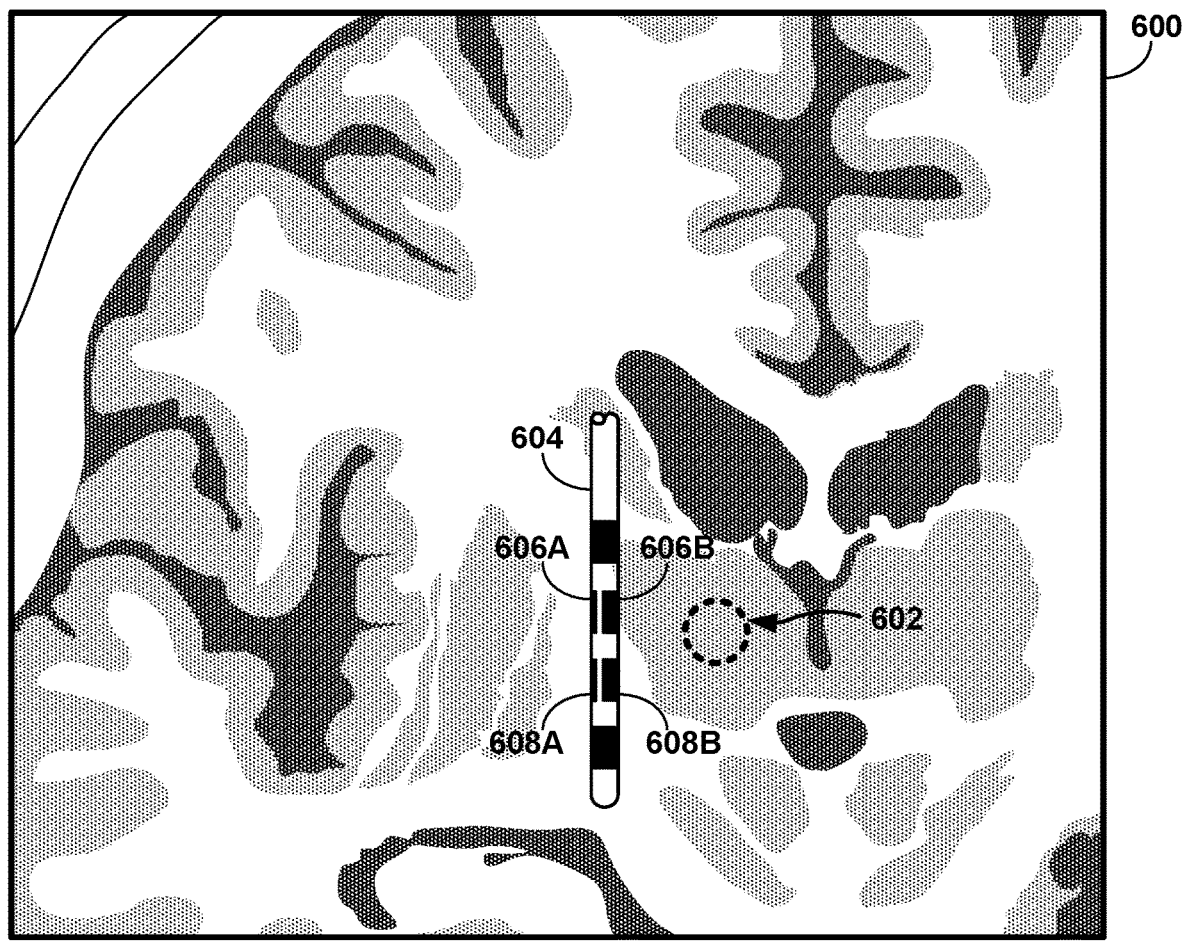
FIG. 6 is a coronal view of example tissue with a lead placed with respect to a target location within tissue.

FIG. 6 is a coronal view of example tissue with a lead 604 placed with respect to a target location within tissue. As shown in FIG. 6, a representation of anatomical regions of brain 120 is displayed by coronal view 600. Coronal view 600 is a front-back vertical section of brain 120. Coronal view 600 may be an actual image of brain 120 produced with magnetic resonance imaging (MRI), computed tomography (CT), or another imaging modality. Coronal view 600 may be an illustration of the location of a lead with respect to a target tissue from which electrical signals originate (e.g., LFP signals). In some examples, coronal view 600 may be presented by programmer 104 or another device to indicate the relative position of lead 604 and the electrodes carried by the lead according to the sensed electrical signals. These images thus may be used to produce the anatomical regions needed to help the clinician program the stimulation parameters.

Coronal view 600 is a 2D coronal slice of brain 120. Differently shaded portions of coronal view 92 indicate varying densities of tissue within brain 120. Darker portions indicate less dense tissue. For example, the darkest portion of coronal view 600 is indicative of spaces within brain 120 that contain cerebral spinal fluid (CSF). White portions of brain 120 indicate dense tissue and more neurons. It should be noted that coronal view 600 is only an example, and actual images may include a wider range of shades and higher image resolution. Coronal view 600 provides a first perspective of the lead and the anatomical region in which the lead is implanted.

As shown in FIG. 6, lead 604 may be a lead icon that represents an actual lead implanted within patient 112. Lead 604 includes electrodes such as electrodes 606A and 606B located at the same longitudinal position and different circumferential positions around the perimeter of lead 604. Electrode 606C cannot be seen because it is located in the backside of lead 604. Similarly, lead 604 includes electrodes such as electrodes 608A and 608B located at the same longitudinal position and different circumferential positions around the perimeter of lead 604. Electrode 608C cannot be seen because it is located in the backside of lead 604. When electrical signals, such as LFP signals originate from target tissue 602, the largest amplitude and power of the signal will likely be sensed by the electrode or electrodes closest to target tissue 602, as this location may be associated with the largest therapeutic window. In this example, a sensing electrode combination of electrodes 606B and 608B may have the largest therapeutic window due to the location to target tissue 602 than any other electrode combinations on lead 604. In some examples, monopolar sensing may result in electrode 606B sensing the highest therapeutic window of electrical signals from target tissue 602. If lead 604 moves with respect to tissue, a different electrode, such as electrode 606A (for lead rotation) or electrode 608B (for longitudinal lead movement), may no longer have the largest therapeutic window.

Figure 7:
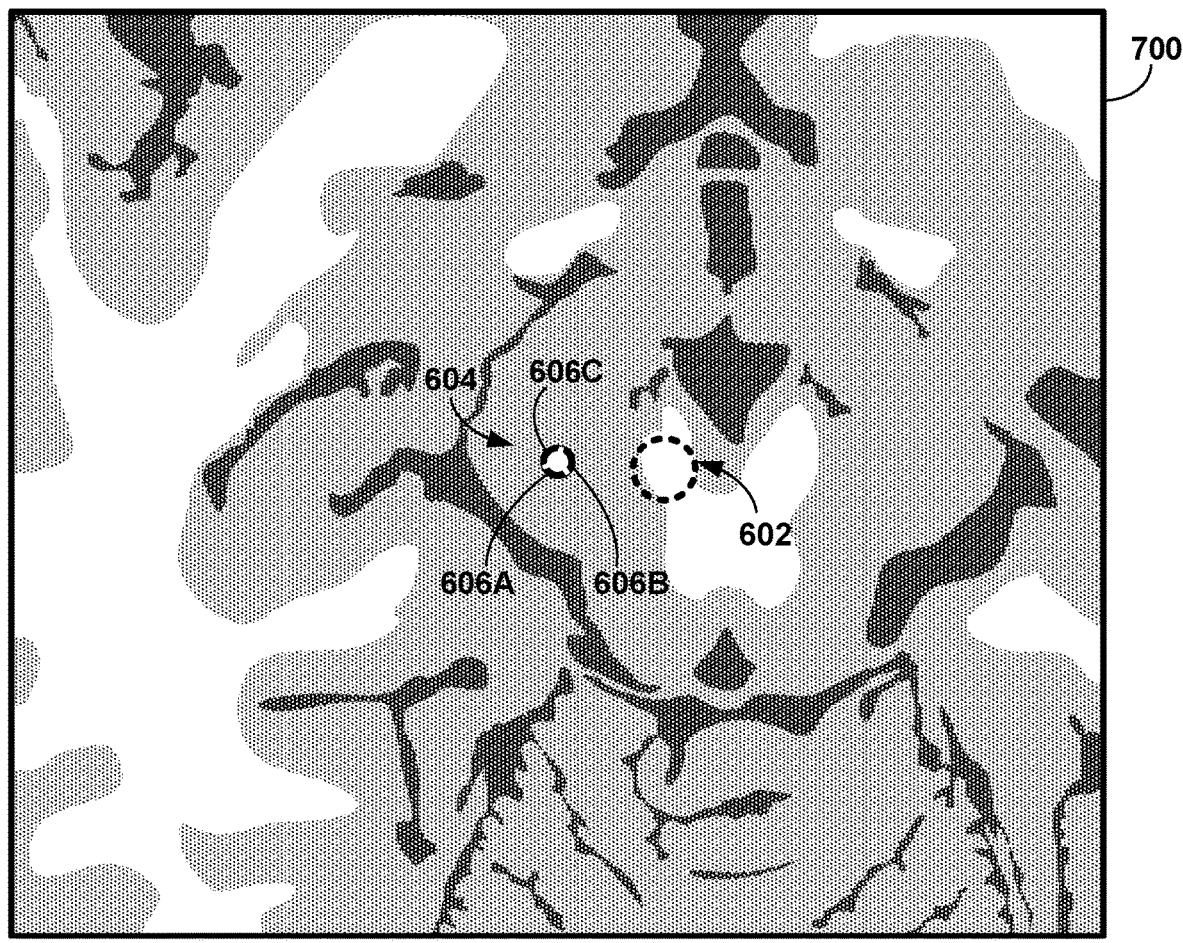
FIG. 7 is an axial view of example tissue with a lead placed with respect to a target location within tissue.

FIG. 7 is an axial view of example tissue with a lead 604 placed with respect to a target tissue 602. Axial view 700 is a different view of tissue than coronal view 600. Axial view 700 also shows the cross-sectional view of lead 604 and electrodes 606A, 606B, and 606C. As shown in axial view 700, electrode 606B is closest to target tissue 602 and may register the largest therapeutic window when compared to the remaining electrodes of lead 604. If lead 604 were to rotate within tissue due to patient movement, lead pull, or some other force, a different electrode, such as electrode 606A, may be located closest to target tissue 602 and sense electrical signals with the largest therapeutic window when compared to other electrodes. Lead 604 may rotate due to other factors as well, such as infection, subdural hematoma, stroke, seizure, post-implant tissue swelling, inflammation, relaxation of frictional sheer-forces between tissue and lead, changes in polymer properties, residual coiling forces in lead wiring, or any other causes. Although FIGS. 6 and 7 discuss electrical signals that may originate in tissue, the same spatial origin may be used when sensing electrical signals evoked from delivered stimulation or sensing delivered stimulation itself for determining lead movement.

Figure 8A:
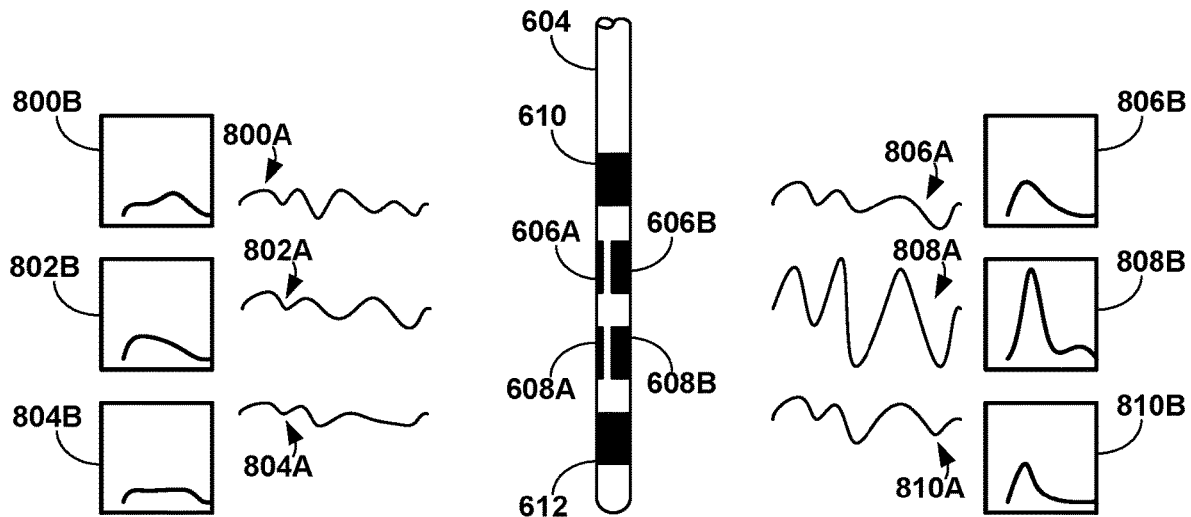
FIGS. 8A, 8B, 8C, and 8D are conceptual views of an example lead with example initial information and signal information recorded from respective electrode combinations.

FIGS. 8A, 8B, 8C, and 8D are conceptual views of an example lead 604 with example initial information and signal information recorded from respective electrode combinations. The signals described in FIGS. 8A-8D may be used to determine stimulation parameters or ranges of parameters, such as a therapeutic window. As shown in FIG. 8A, initial information may represent electrical signals sensed at a first time when lead 604 is in a first position with respect to tissue. The initial information may include one or more characteristics of the sensed electrical signals at the first time. The one or more characteristics may include some aspect of the electrical signals that can be used to compare the electrodes to each other over time. For example, the characteristic may be an amplitude of the sensed signal (e.g., absolute amplitude, a normalized amplitude, a categorized amplitude (e.g., amplitude values fall within separate pre-determined ranges), or a ranked amplitude). This amplitude may be the maximum amplitude over a period of time, for example. In other examples, the characteristic may be a differential signal between electrodes or a spatial derivative (e.g., first or second spatial derivative) in the axial and/or angular directions to estimate the proximity of each electrode to a signal source. For example, the second spatial derivative may provide information regarding how fast the signal amplitudes change to provide an indication of proximity of that electrode or electrode combination to the signal source. In other examples, a full two dimensional or three dimensional Laplacian can be employed for simultaneous recording across electrodes for the characteristic of each electrode and compared over time to estimate movements of lead 604 in all directions (e.g., rotational and shifting movements).

In some examples, the characteristic may be a relative phase between electrodes. The relative phase may differentiate between multiple tissue signal sources that may be out of phase with each other. IMD 106 may thus analyze the relative phase for each electrode or electrode combination and determine the orientation of the electrode(s) with respect to the signal source or sources. The relative phase may be employed by IMD 106 to improve the confidence in the lead orientation or lead movement determination in some examples. In other examples, the characteristic may be a spectral power. The spectral power may be a power (e.g., absolute or normalized amplitude) for one or more frequency bands of the electrical signal. For example, IMD 106 may calculate the power of the beta frequency band for each sensed electrical signal, which may indicate the proximity of each electrode combination to a target neural location expected to generate signals in the beta frequency band. IMD 106 may select the frequency bad as generic for all patients or patient specific sensed signals. For example, the patient-specific frequency band may be selected to have a window centered around an identified peak in the spectrum (e.g., plus and minus 5 Hz from the identified peak). In other examples, IMD 106 may determine a rank for each electrode or electrode combination for any of the above-referenced parameters to determine if the rank of the electrodes changes between measurements. In this manner, the initial information (and signal information) may include determined characteristics representative of one or more aspects of the sensed electrical signals. In addition, or alternatively, the initial information (and signal information) may include at least a portion of the sensed electrical signal waveform for comparison to a template, threshold, or some other function enabling comparison of the electrical signals sensed by different electrode combinations. Any of these characteristics may be used alone or in combination with other characteristics to identify electrode position with respect to a signal source and/or lead movement over time. In addition, any of these characteristics may be employed by IMD 106 to determine x, y, and z or r, theta, and z coordinates, depending on the desired coordinate system, of the signal source. IMD 106 may then determine the coordinates of the signal source at multiple different times to identify any changes to the coordinates representative of lead movement (e.g., shift or rotation). In some examples, IMD 106 may perform corrections to sensed signals or include circuitry that balances impedance difference between electrodes of different sizes. This differences in impedances may alter the sensed signals and distort the determined distances to the signal source. IMD 106 may also compute corrections for different spacing between electrodes of different electrode combinations. For example, larger distances between electrodes similarly increases the amplitude of the sensed voltage. In order to compare signals from one electrode combination to another electrode combination with different spacing, IMD 106 may correct (or normalize) the sensed signal amplitude to compensate for these different spacings.

As shown in the example of FIG. 8A, waveform amplitudes 800A, 802A, 804A, 806A, 808A, and 810A (collectively "waveform amplitudes") are examples of initial information. Spectral powers 800B, 802B, 804B, 806B, 808B, and 810B (collectively "spectral powers") are additional, or alternative, examples of initial information. Each of the waveform amplitudes and spectral powers are determined from electrical signals sensed by a respective electrode combination. In the position of lead 604 as shown in the example of FIG. 8A, electrodes 606B and 608B are located on one side of lead 604 to detect signals such as waveform amplitudes 806A, 808A, and 810A and spectral powers 806B, 808B, and 810B. Conversely, electrodes 606A and 608A are located on a different side of lead 604 to detect signals such as waveform amplitudes 800A, 802A, and 804A and spectral powers 800B, 802B, and 804B. IMD 106 or another device may generate each of the spectral powers by analyzing the power of the frequencies present in the respective waveform amplitudes (e.g., spectral power 800B is generated by waveform amplitude 800A).

Each of the signals shown in FIG. 8A can be attributed to the signal sensed between an electrode combination of two electrodes. For example, IMD 106 may generate waveform amplitude 800A and/or spectral power 800B based on the electrical signal sensed between electrodes 610 and 606A. Similarly, IMD 106 may generate waveform amplitude 802A and/or spectral power 802B based on the electrical signal sensed between electrodes 606A and 608A and generate waveform amplitude 804A and/or spectral power 804B based on the electrical signal sensed between electrodes 608A and 612. Since electrodes 606A or 608A are part of the electrode combinations used to generate these signals, IMD 106 can determine that those signals originate from tissue in the direction of electrodes 606A or 608A. The same is true for other electrodes located at different positions around the perimeter of lead 604, such as electrodes 606B and 608B. Electrodes 606C and 608C are on the backside of lead 604 and cannot be viewed in the example of FIG. 8A. Therefore, IMD 106 may generate waveform amplitude 806A and/or spectral power 806B based on the electrical signal sensed between electrodes 610 and 606B. Similarly, IMD 106 may generate waveform amplitude 808A and/or spectral power 808B based on the electrical signal sensed between electrodes 606B and 608B and generate waveform amplitude 810A and/or spectral power 810B based on the electrical signal sensed between electrodes 608B and 612.

IMD 106 may monitor the signals sensed by the different electrode combinations over time to determine when the sensed signals, or characteristics of those signals, has changed indicating that lead 604 has rotated about the longitudinal axis and/or shifted along the longitudinal axis. For example, the largest waveform amplitude and the largest spectral power as shown in FIG. 8A was waveform amplitude 808A and spectral power 808B from the signals sensed by the electrode combination of electrodes 606B and 608B. This larger amplitude may indicate that the tissue of interest is closest to electrodes 606B and 608B than any other electrodes of lead 604. In other examples, there may not be a tissue of interest. Instead, IMD 106 may use one or more of the characteristics of the signals sensed by the respective electrode combinations to establish a baseline pattern of signals that indicates an initial position in tissue of lead 604. IMD 106 may use this initial baseline pattern to detect changes in the signals sensed from one or more electrode combinations indicative of electrode movement with respect to tissue.

Figure 8B:
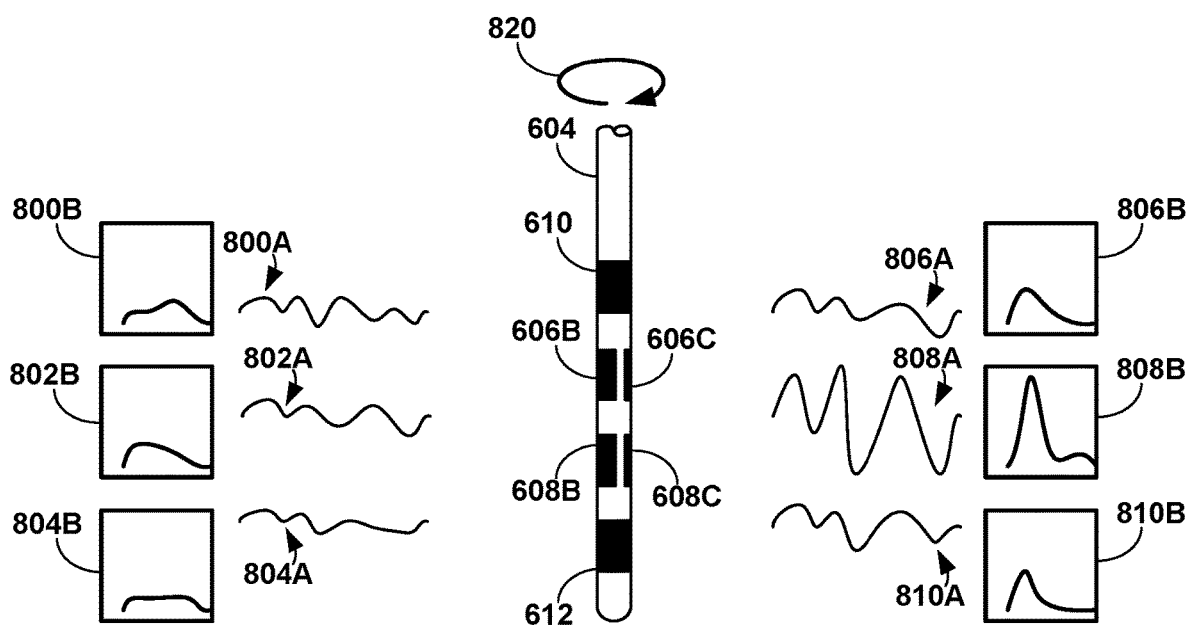

As shown in FIG. 8B, lead 604 has rotated in the direction of arrow 820 such that the electrode combinations of lead 604 sense different electrical signals in the new position of FIG. 8B than in the example of FIG. 8A. For example, IMD 106 may generate waveform amplitude 800A and/or spectral power 800B based on the electrical signal sensed between electrodes 610 and 606B. Similarly, IMD 106 may generate waveform amplitude 802A and/or spectral power 802B based on the electrical signal sensed between electrodes 606B and 608B and generate waveform amplitude 804A and/or spectral power 804B based on the electrical signal sensed between electrodes 608B and 612. Likewise, IMD 106 may generate waveform amplitude 806A and/or spectral power 806B based on the electrical signal sensed between electrodes 610 and 606B, generate waveform amplitude 808A and/or spectral power 808B based on the electrical signal sensed between electrodes 606C and 608C, and generate waveform amplitude 810A and/or spectral power 810B based on the electrical signal sensed between electrodes 608C and 612. IMD 106 may thus identify that the largest amplitude of waveform amplitude 808A or spectral power 808B is now associated with the electrode combination of electrodes 606C and 608C instead of by electrodes 606B and 608B. IMD 106 may thus identify that lead 604 has rotated in the direction of arrow 820. IMD 106 may thus adjust electrode combinations used to deliver therapy, adjust other therapy parameter values, initiate a reprogramming of therapy parameters, turn off therapy, or initiate an alert in response to determining that lead 604 has rotated with respect to tissue.

Although the same waveform amplitudes and spectral powers are shown in FIGS. 8A and 8B for illustrative purposes, the waveform amplitudes, spectral powers, or other characteristics of sensed electrical signals may be different between different electrode combinations as a result of lead movement. For example, after lead 604 rotates, electrodes 606C and 608C may not sense the same electrical signals as sensed by electrodes 606B and 608B prior to the rotation. However, IMD 106 may track the electrode combination that senses the largest waveform amplitude or spectral power, or a pattern of amplitudes, or identify when lead 604 has rotated. In addition, the sensed signals shown in FIGS. 8A-8D may be used to generate the therapeutic windows for each electrode or electrode combination, and the therapeutic windows can be used to determine which electrodes should be used for stimulation, whether the lead has moved, or whether there is disease progression or changes.

IMD 106 may analyze any changes to the characteristics of electrical signals sensed by the electrode combinations to determine movement of lead 604 with respect to tissue in any direction. Using the techniques described herein, IMD 106 may determine that lead 604 rotated in tissue or shifted up or down along the longitudinal axis of lead 604. For example, IMD 106 may determine that the largest waveform amplitude is detected by the electrode combination of electrodes 608B and 612 instead of electrodes 606B and 608B to determine that lead 604 has shifted proximally. IMD 106 may continually monitor electrode signals over time to identify additional movements of lead 604, such as rotations or shifts of lead 604 with respect to tissue. IMD 106 may determine lead movements based on electrical signals sensed by electrodes on any array of electrodes, which may encompass, one, two, three, or more separate leads. In this manner, IMD 106 may monitor any group of electrode combinations to determine when the electrodes have moved with respect to tissue.

The example characteristics of the sensed electrical signals between electrodes of an electrode combination are the waveform amplitudes and spectral powers shown in FIGS. 8A and 8B. However, IMD 106 may determine lead rotation based on different characteristics of electrical signals. For example, IMD 106 may determine lead movement based on changes to impedances sensed for one or more electrode combinations. IMD 106 may sense impedance between at least two electrodes of respective electrode combinations. Since the sensed impedance is affected by tissue between the electrodes, IMD 106 may determine lead rotation based on changes to the sensed impedance of one or more electrode combinations.

Figure 8C:
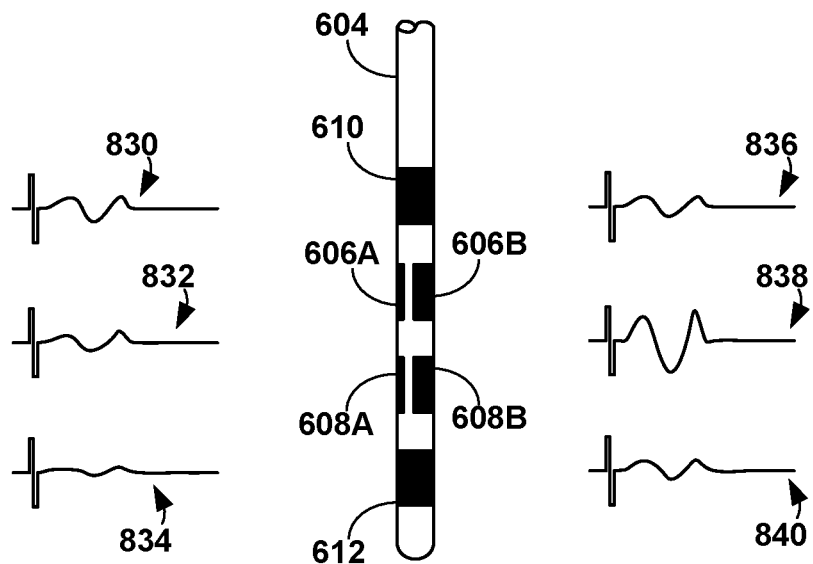

Other types of sensed signals or characteristics may be used by IMD 106 or another device to determine lead movement. As shown in FIG. 8C, IMD 106 may determine lead movement based on changes to sensed evoked responses (e.g., one or more characteristics of a physiologically generated electrical signal, such as an evoked compound action potential (ECAP)) sensed by one or more electrode combinations. Another type of evoked signal may be an evoked resonant neural activity (ERNA) signal. IMD 106 may generate an electrical stimulus (e.g., a pulse or other waveform) via two or more electrodes on lead 604 or another lead. The electrical stimulus may be defined by stimulation parameters selected to elicit a nerve response that is detectable by electrodes on lead 604. A characteristic of the evoked signal, such as the amplitude of the nerve response may be proportional to the distance from the stimulus electrodes and the nervous tissue and the distance from the nervous tissue and the sensing electrodes. Therefore, the amplitude of the sensed evoked signal may be indicative of how far the sensing electrodes are from the nervous tissue and whether or not the electrodes have moved with respect to the tissue. IMD 106 may sense evoked signals from all electrode combinations based on a single stimulus or sense evoked signals for each electrode combination from respective stimuli. IMD 106 may sense the evoked response on the same lead or a different lead than the lead which delivered the stimulation that elicited the evoked response. When stimulation is delivered by electrodes on one lead and evoked signals are sensed by electrodes on another lead, IMD 106 may determine from the sensed evoked signals whether the stimulation lead or the sensing lead has moved with respect to tissue.

For example, IMD 106 may generate waveform signal 830 based on the electrical signal sensed between electrodes 610 and 606A as a result of the delivered stimulus. Each sensed waveform signal, such as waveform signal 830, may include a first biphasic square wave pulse (e.g., an artifact representing the delivered stimulus) followed by the evoked signal from stimulated neural tissue. Similarly, IMD 106 may generate waveform signal 832 based on the electrical signal sensed between electrodes 606A and 608A and generate waveform signal 834 based on the electrical signal sensed between electrodes 608A and 612. Likewise, IMD 106 may generate waveform signal 836 based on the electrical signal sensed between electrodes 610 and 606B, generate waveform signal 838 based on the electrical signal sensed between electrodes 606B and 608B, and generate waveform signal 840 based on the electrical signal sensed between electrodes 608B and 612.

IMD 106 may analyze the amplitude, area under the curve, or other characteristic of at least a portion of the evoked waveform following the artifact. For example, the sensed signal may include multiple peaks of alternating polarities, and IMD 106 may analyze one or more of any of the peaks of the sensed signal. Similar to the waveform amplitude or spectral power discussed above, IMD 106 may monitor for changes to the evoked waveform characteristic, such as amplitude, over time. If the lead has moved, the sensed evoked response will change for one or more electrode combinations because the distance between the stimulus electrode(s) and the evoked tissue and/or the distance between the sensing electrodes and the evoked tissue will have changed. For example, evoked waveform 838 has the largest amplitude as sensed by electrodes 606B and 608B. If IMD 106 then determines that the electrode combination of electrodes 606A and 608A senses an evoked waveform that has the largest amplitude of all electrode combinations, then IMD 106 may determine that lead 604 has rotated such that electrodes 606A and 608A are now closer to the neuronal tissue than electrodes 606B and 608B.

Figure 8D:
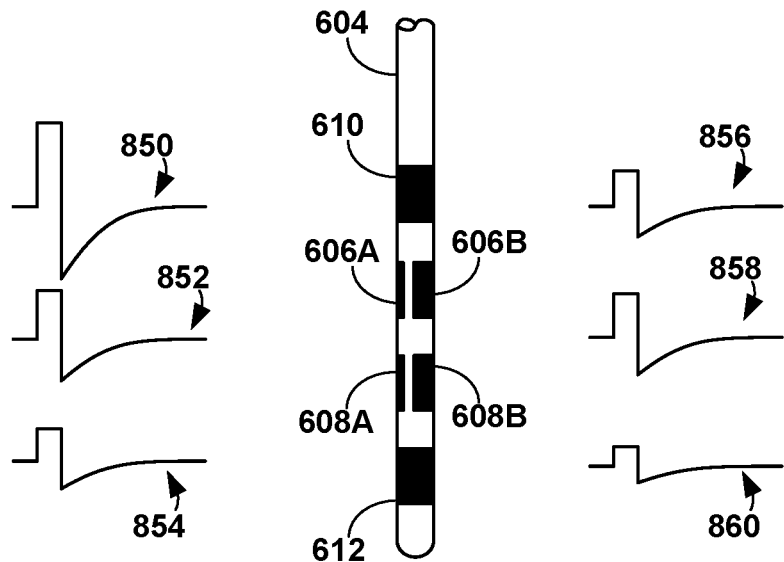

FIG. 8D illustrates another technique for determining lead movement that is similar to the evoked waveforms used in FIG. 8C. However, IMD 106 may determine lead movement based on changes to sensed electrical stimulus itself from one or more distant electrodes. IMD 106 may generate the electrical stimulus from an electrode on a housing of IMD 106, an electrode on a different lead, or control a different device (external or internal device) to deliver the electrical stimulus. IMD 106 may sense the electrical stimulus from one or more electrical combinations on lead 604, and this sensed signal may be referred to as an artifact or pulse because it is not physiological in origin. Nonetheless, electrodes closest to the origin of the electrical stimulus may sense the stimulus as a larger amplitude, indicative of the orientation of lead 604 with respect to the location of the electrical stimulus.

For example, IMD 106 may generate sensed signal 850 based on the electrical signal sensed between electrodes 610 and 606A indicative of the delivered stimulus. Each sensed signal, such as sensed signal 850, may include a first biphasic square wave pulse (e.g., an artifact representing the delivered stimulus). Similarly, IMD 106 may generate sensed signal 852 based on the electrical signal sensed between electrodes 606A and 608A and generate sensed signal 854 based on the electrical signal sensed between electrodes 608A and 612. Likewise, IMD 106 may generate sensed signal 856 based on the electrical signal sensed between electrodes 610 and 606B, generate sensed signal 858 based on the electrical signal sensed between electrodes 606B and 608B, and generate sensed signal 860 based on the electrical signal sensed between electrodes 608B and 612. In the example of FIG. 8D, the largest sensed amplitude may be from sensed signal 850 from electrodes 606A and 610. If subsequent sensed signals indicate that a different electrode combination senses a signal with the largest amplitude, then IMD 106 may determine that lead 604 has moved in accordance with the different electrode combination sensing the largest amplitude sensed signal.

In this manner, if IMD 106 or another device delivers an electrical stimulus from an electrode not part of lead 604, for example, the electrode combinations of lead 604 will sense that delivered electrical stimulus with different respective amplitudes based on the orientation of the electrodes of each electrode combination with respect to the stimulus electrode. If the lead has moved, the sensed stimulus amplitude will change for one or more electrode combinations because the distance between the stimulus electrode(s) and sensing electrodes of each electrode combination will have changed. IMD 106 may use any of these, or combinations of these, sensing techniques in order to determine movement of electrodes of a lead with respect to tissue.

In some examples, IMD 106, an external system (e.g., a lead trialing system), and/or a physician may implement the techniques described herein to intraoperatively rotate and/or shift the position of the lead to a target location with respect to surrounding anatomy. For example, the physician or surgical robot may rotate and/or shift the lead until an electrode, or electrode combination, is directly positioned to record the largest therapeutic window. This positioning during implantation may enable the physician to improve the available therapeutic window (e.g., the greatest difference in amplitude between the minimum amplitude that provides therapy and the maximum amplitude that elicits side effects). This positioning may also reduce the electrical current requires to provide effective therapy. To enable this intra-operative positioning technique, the lead may be connected to a trialing system similar to IMD 106, the IMD 106 itself, or an external recording system. If the lead is not directly connected to IMD 106, the physician may connect the lead to IMD 106 once positioned.

Figure 9A:
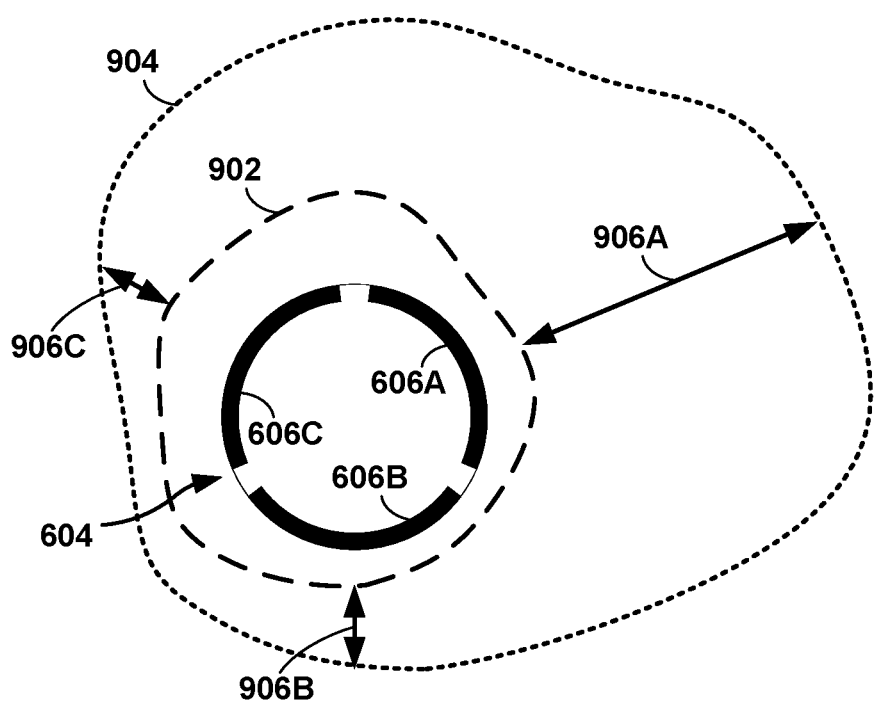
FIGS. 9A and 9B are conceptual illustrations of example therapeutic windows between different rotational positions of the lead.
Figure 9B:
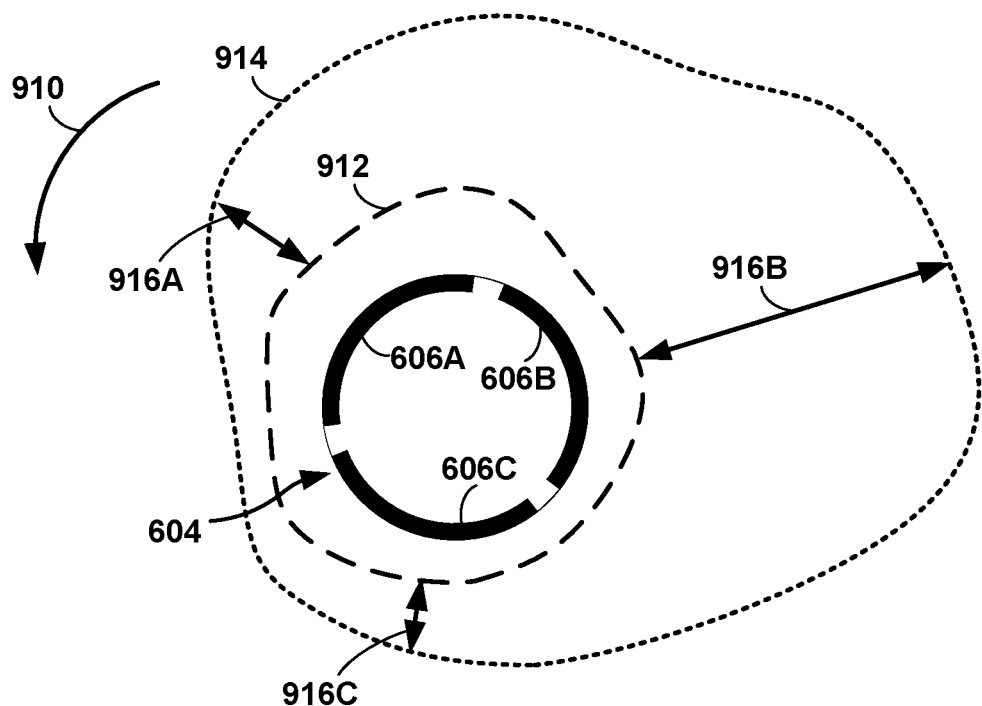

FIGS. 9A and 9B are conceptual illustrations of example therapeutic windows between different rotational positions of the lead. As shown in FIG. 9A, lead 604 includes electrodes 606A, 606B, and 606C located at different positions around lead 604. Based on the sensed signals from each of the electrodes 606, IMD 106 may generate the lower therapeutic threshold 902 around the perimeter of lead 604. For example, the lower therapeutic threshold 902 may correspond to the stimulation amplitude above which symptoms are suppressed for the patient. Based on the sensed signals from each of the electrodes 606, IMD 106 may also generate the upper therapeutic threshold 904 around the perimeter of lead 604. For example, the upper therapeutic threshold 904 may correspond to the stimulation amplitude above which stimulation produces undesirable side effects.

The amplitude difference between upper therapeutic threshold 904 and lower therapeutic threshold 902 at any given location is referred to as the therapeutic window in this example. For example, therapeutic windows 906A, 906B, and 906C represent the therapeutic window at each spatial location of the respective arrows. In the example of FIG. 9A, therapeutic window 906A would correspond to the largest therapeutic window and is associated with stimulation via electrode 606A which could be selected for therapy.

In the example of FIG. 9B, the lead has rotated in the direction of arrow 910. However, the general shape of lower therapeutic threshold 912 around the perimeter of lead 604 and the general shape of upper therapeutic threshold 914 around the perimeter of lead 604 are similar to that of FIG. 9A. Therefore, IMD 106 may determine that there is no physiological change. Instead, the electrodes 606A, 606B, and 606C are associated with different therapeutic windows 916A, 916B, and 916C than in FIG. 9A. For example, the therapeutic window 916B sensed by electrode 606B may be similar to the therapeutic window 906A sensed by electrode 606A. Due to this change, and the similar changes for electrodes 606A and 606C, IMD 106 may determine that lead 604 has rotated in the direction of arrow 910.

Figure 10A:
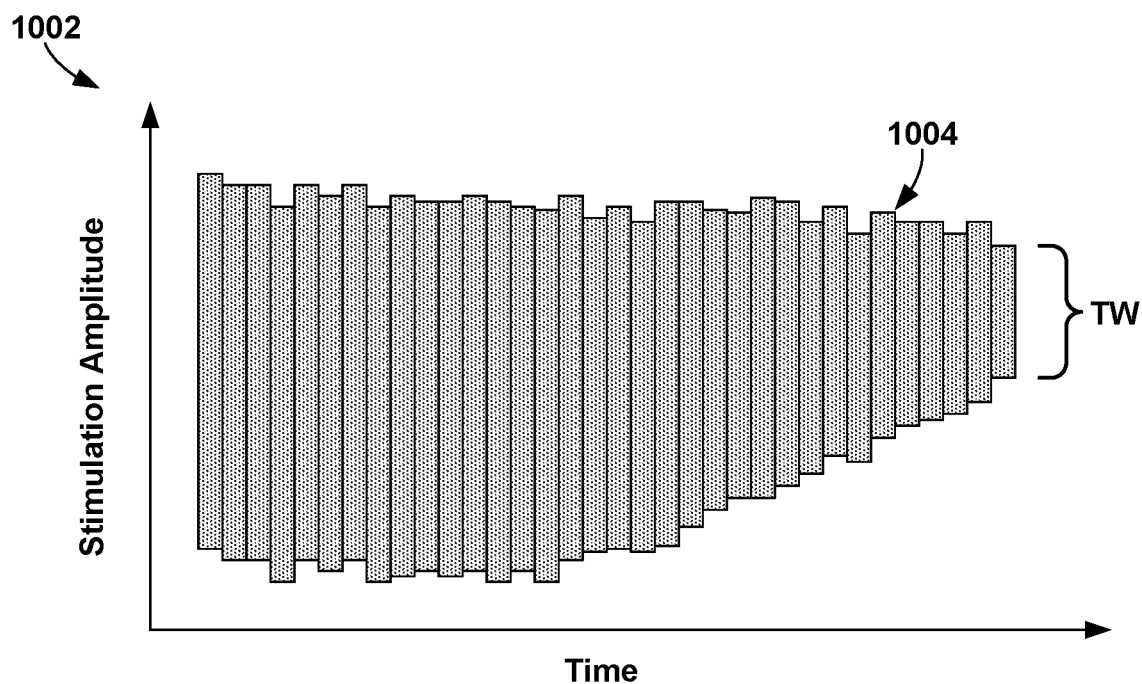
FIGS. 10A and 10B are graphs illustrating example therapeutic window changes over time for respective electrode combinations indicating lead rotation.
Figure 10B:
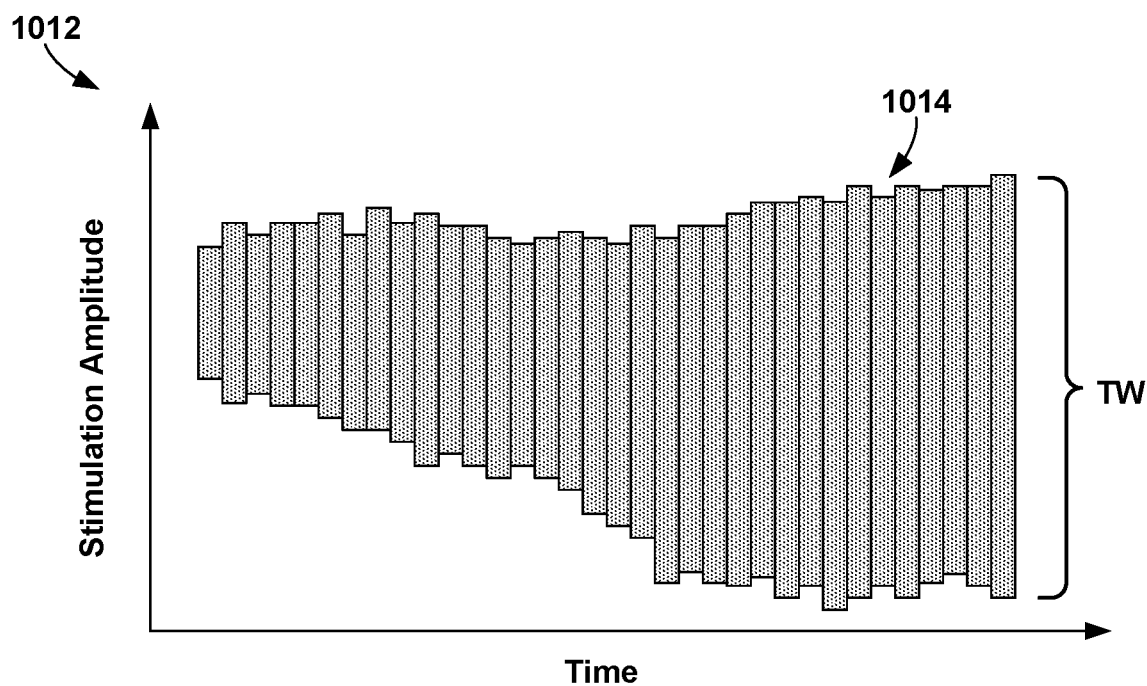

FIGS. 10A and 10B are graphs illustrating example therapeutic window changes over time for respective electrode combinations indicating lead rotation. For example, graph 1002 may correspond to the therapeutic window determined for electrode 606A in FIGS. 9A and 9B, and graph 1012 may correspond to the therapeutic window determined for electrode 606B in FIGS. 9A and 9B. As shown in FIG. 10A, the therapeutic window amplitude 1004 decreases over time. However, over the same time period, the therapeutic window amplitude 1014 in FIG. 10B increases to a similar extent over time. Due to this exchange in therapeutic window amplitudes for electrodes 606A and 606B, IMD 106 may determine that the lead has rotated such that electrode 606B is now associated with the larger and more preferred therapeutic window. IMD 106 may responsively change the electrode combination used for stimulation, for example.

Figure 11A:
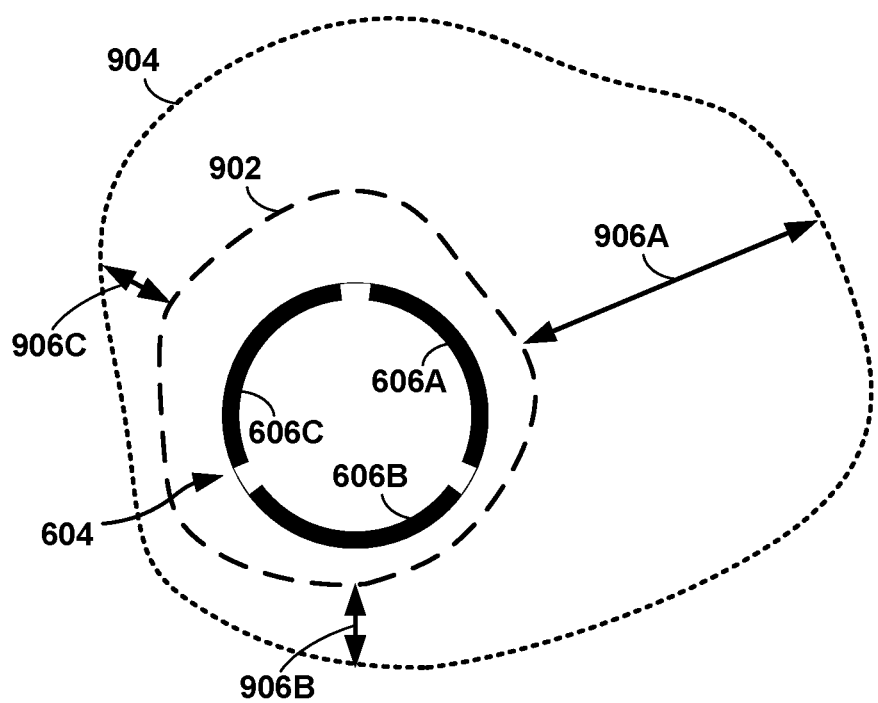
FIGS. 11A and 11B are conceptual illustrations of example therapeutic windows that change due to changing physiological states for the patient.
Figure 11B:
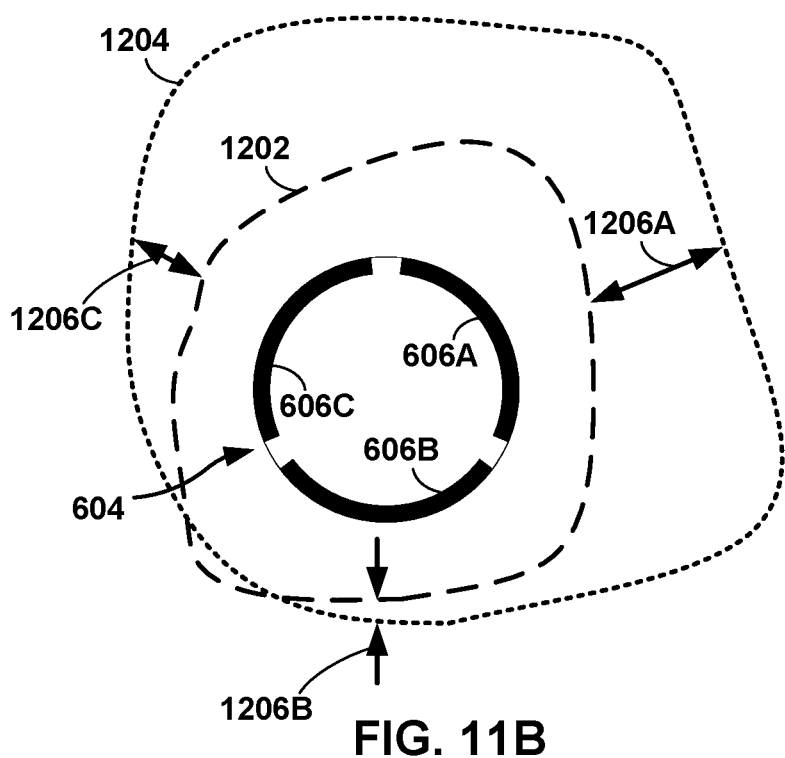

FIGS. 11A and 11B are conceptual illustrations of example therapeutic windows that change due to changing physiological states for the patient. As shown in FIG. 11A, lead 604 includes electrodes 606A, 606B, and 606C located at different positions around lead 604. Based on the sensed signals from each of the electrodes 606, IMD 106 may generate the lower therapeutic threshold 902 around the perimeter of lead 604. For example, the lower therapeutic threshold 902 may correspond to the stimulation amplitude above which symptoms are suppressed for the patient. Based on the sensed signals from each of the electrodes 606, IMD 106 may also generate the upper therapeutic threshold 904 around the perimeter of lead 604. For example, the upper therapeutic threshold 904 may correspond to the stimulation amplitude above which stimulation produces undesirable side effects. The amplitude difference between upper therapeutic threshold 904 and lower therapeutic threshold 902 at any given location is referred to as the therapeutic window in this example. For example, therapeutic windows 906A, 906B, and 906C represent the therapeutic window at each spatial location of the respective arrows. In the example of FIG. 11A, therapeutic window 906A would correspond to the largest therapeutic window and is associated with stimulation via electrode 606A which could be selected for therapy.

In the example of FIG. 11B, the general shape of lower therapeutic threshold 1202 around the perimeter of lead 604 and the general shape of upper therapeutic threshold 1204 around the perimeter of lead 604 have changed with respect to the upper and lower therapeutic thresholds of FIG. 11A. Therefore, IMD 106 may determine that there has been a physiological change from the initial state in FIG. 11A to an altered state in FIG. 11B. Since the amplitudes of all of therapeutic windows 1206A, 1206B, and 1206C have decreased compared to therapeutic windows 906A, 906B, and 906 of FIG. 11A, IMD 106 can identify that the physiological change is disease degeneration. Smaller therapeutic windows typically represent progression of disease because there is a smaller range of therapeutic amplitudes available.

Figure 12:
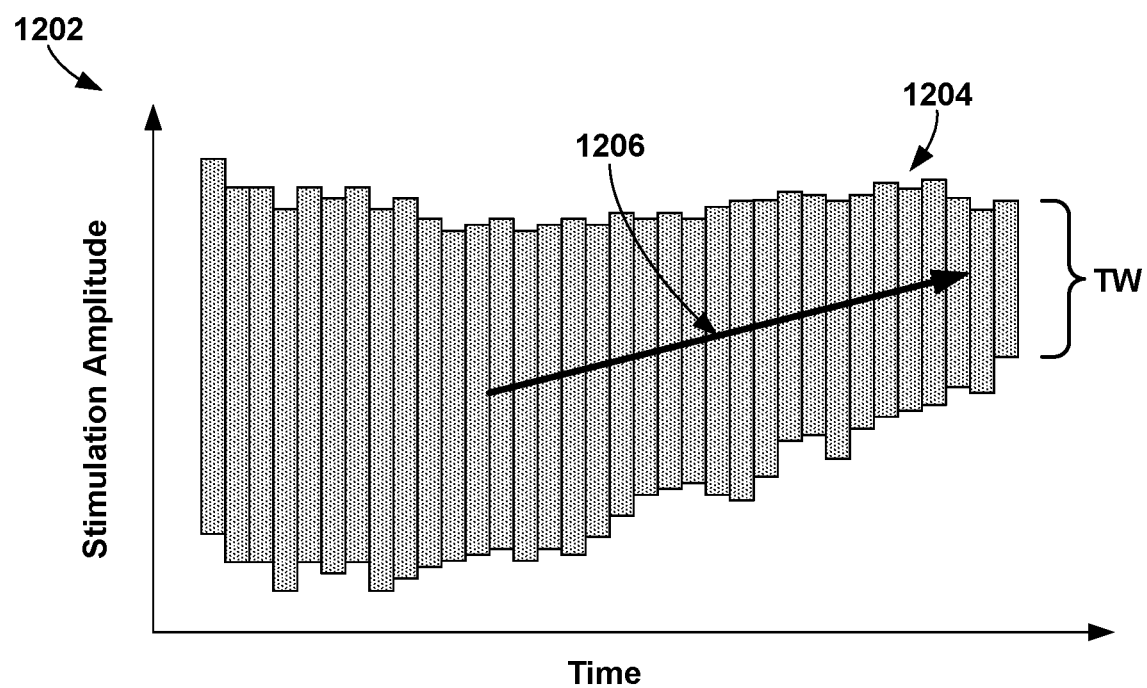
FIG. 12 is a graph illustrating example therapeutic window changes over time for respective electrode combination indicating changing physiological states and disease progression.

FIG. 12 is a graph illustrating example therapeutic window changes over time for respective electrode combination indicating changing physiological states and disease progression. For example, graph 1202 may correspond to the therapeutic window determined for electrode 606A in FIGS. 11A and 11B. As shown in FIG. 12, the therapeutic window amplitude 1204 decreases over time. In addition, there is a trend 1206 that increases over time indicative of a need to increase stimulation amplitude in order to suppress symptoms for the patient. Although both of these reduction to therapeutic window amplitude and increase in trend 1206 may indicate disease progression, only one or the other may be needed for IMD 106 to make that determination. Further, IMD 106 may determine that disease progression has occurred instead of lead movement in response to determining that the therapeutic window has not increased for any other electrode or electrode combination. IMD 106 and/or another device, such as programmer 104, may control a user interface to present a representation that these therapeutic windows have changed over time and/or that the disease is progressing, the disease is stable, or the disease is improving. In some examples, IMD 106 and/or programmer 104, for example, may determine alternative stimulation parameters and/or times for stimulation that may be appropriate to address any changes to the disease progression.

Although FIGS. 9A-12 discuss identifying a change in disease using a changing therapy window of amplitude and/or trend in amplitude, the system may utilize other stimulation parameters in addition or as an alternative to amplitude. For example, the system may monitor stimulation frequency changes that are made over time. These stimulation frequency changes may be requested by a clinician or performed by the system in order to maintain effective therapy such as suppression of tremor. In one example, the system may be configured to deliver stimulation at a pulse frequency of 130 Hz. However, as the disease progresses, the clinician or patient may request higher frequencies to maintain reduction of symptoms, or the system may automatically increase the frequency in response to detecting symptoms or receiving user input indicating that symptoms are returning. The system may monitor the stimulation frequency as an indicator of disease progression. For example, instead of the therapy window range changing over time as shown in FIG. 10A, the system may plot the stimulation frequency used over time. Increasing frequency may indicate continued disease progression. No changes to frequency may indicate that the patient is not experiencing worsening of the disease. If the disease worsens, the system may recommend or make changes to one or more stimulation parameters in order to maintain therapy.

Figure 13:
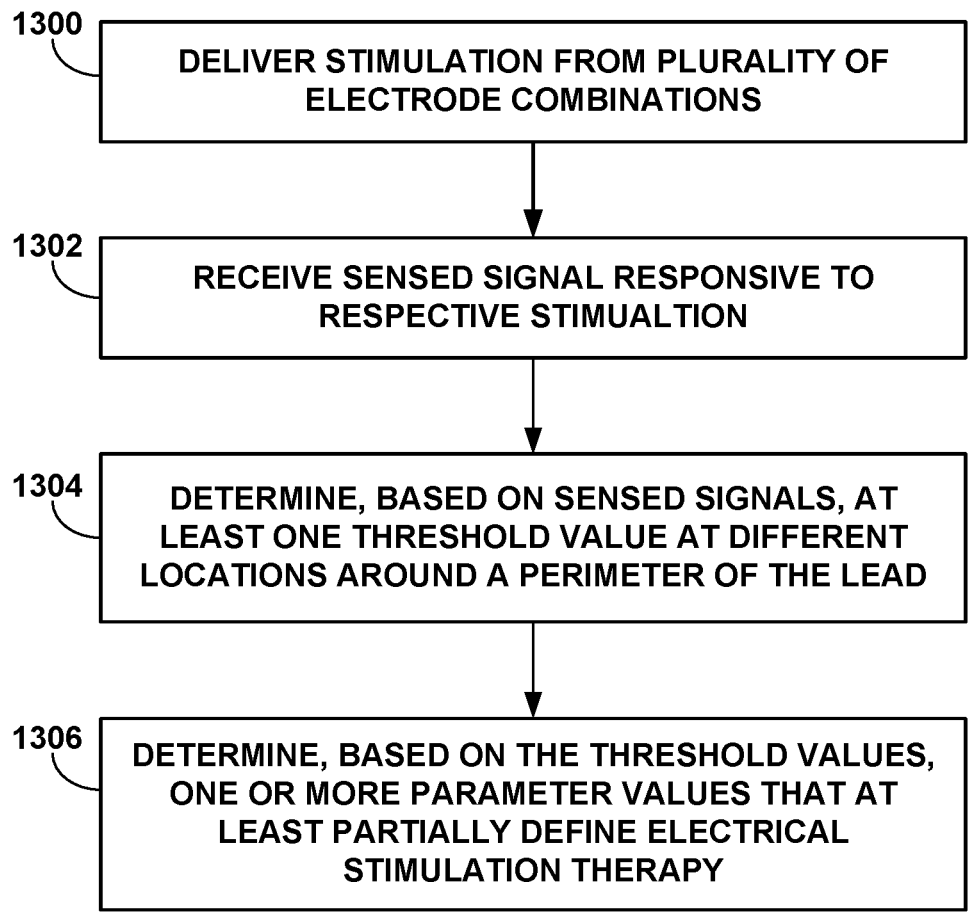
FIG. 13 is a flowchart illustrating an example technique for determining an electrode combination based on one or more threshold values determined for multiple electrodes.

FIG. 13 is a flowchart illustrating an example technique for determining an electrode combination based on one or more threshold values determined for multiple electrodes. The technique of FIG. 13 will be described with respect to processor 210 of IMD 106 in FIG. 2. However, other processors, devices, or combinations thereof, may perform the techniques of FIG. 13 in other examples.

As shown in FIG. 13, processor 210 controls IMD 106 to deliver stimulation from a plurality of electrode combinations (1300). Processing 210 then controls IMD 106 to receive sensed signals responsive to the respective stimulation (1302). Based on the sensed signals, processor 210 determines at least one therapeutic threshold value at different locations around the perimeter of the lead and/or at other axial locations of the lead (1304). The therapeutic threshold values may be values for only a lower therapeutic thresholds, only a higher therapeutic threshold, both upper and lower therapeutic thresholds, or the therapeutic window (which can be calculated based on the difference between the upper and lower therapeutic thresholds). Processing 210 then determines, based on the therapeutic threshold values, one or more parameter values that at least partially define electrical stimulation therapy (1306). The parameter values may be values for amplitude, electrode combination, or any other parameter.

Figure 14:
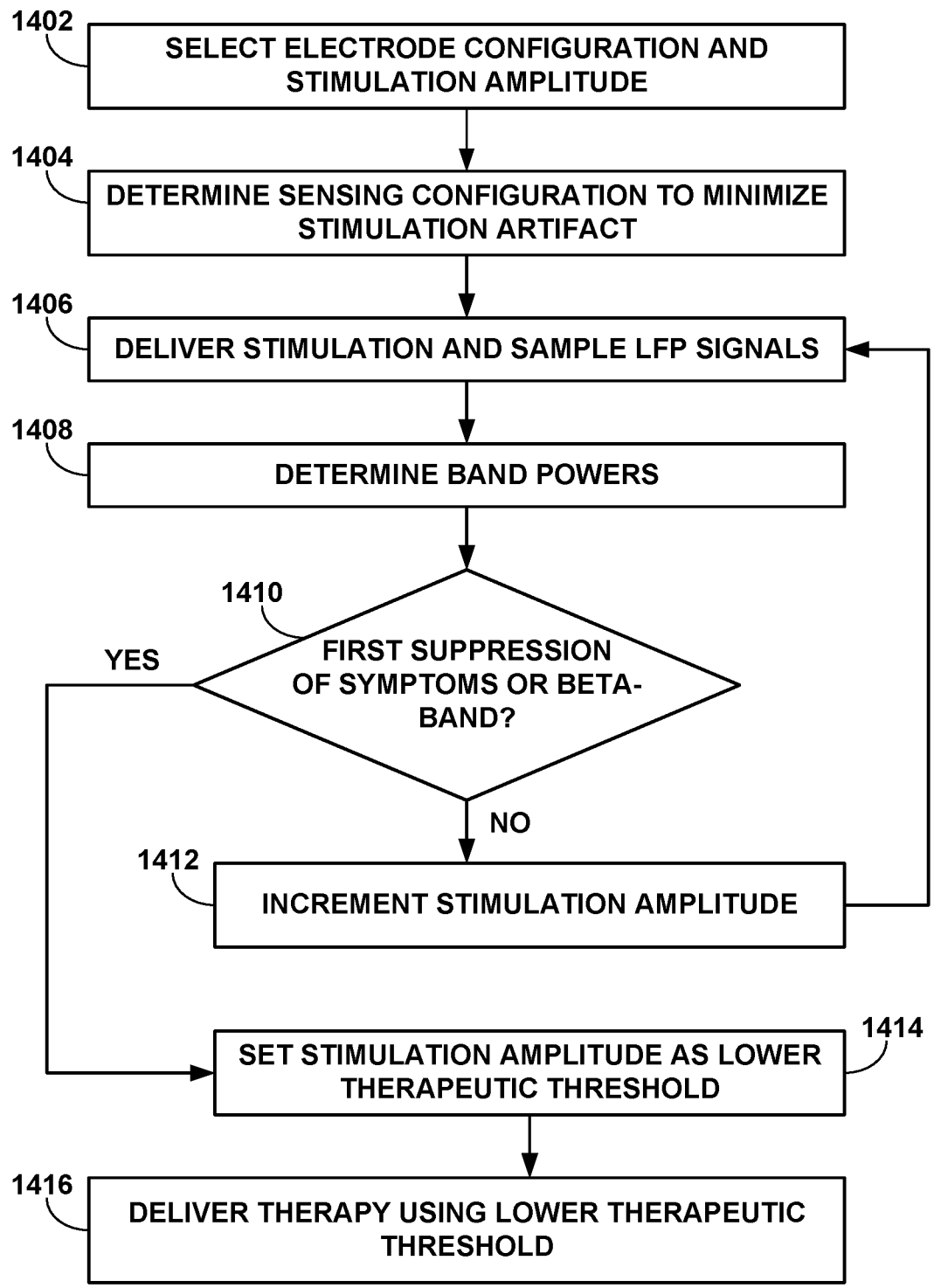
FIG. 14 is a flowchart illustrating an example technique for determining a lower therapeutic threshold for stimulation therapy.

FIG. 14 is a flowchart illustrating an example technique for determining a lower therapeutic threshold for stimulation therapy. The technique of FIG. 14 will be described with respect to processor 210 of IMD 106 in FIG. 2. However, other processors, devices, or combinations thereof, may perform the techniques of FIG. 14 in other examples.

As shown in FIG. 14, processor 210 selects an electrode configuration and an initial stimulation amplitude (1402). Processor 210 then determines the sensing electrode configuration to minimize stimulation artifact (1404) before controlling the delivery of stimulation and sampling of LFP signals (1406). From the LFP signals, processor 210 determines the powers one or more frequency bands (1408). If processor 210 does not determine that there has been a first suppression of symptoms due to a reduction in the beta band power ("NO" branch of block 1410), processor 210 increments the stimulation amplitude (1412) and then controls delivery of stimulation with the new stimulation amplitude (1406). Beta frequency band may be about 13 Hertz to about 30 Hertz.

If processor 210 determines that there has been a first suppression of symptoms due to a reduction in the beta band power ("YES" branch of block 1410), processor 210 sets the current stimulation amplitude as the lower therapeutic threshold (1414). Processor 1416 can then control delivery of therapy using the lower therapeutic threshold, such as using an amplitude that is equal to or greater than the lower therapeutic threshold (1416). Processor 210 may repeat the process of FIG. 14 for each electrode combination as part of an electrode sense sweep, and select an electrode combination with the lowest lower therapeutic threshold for subsequent stimulation.

Figure 15:
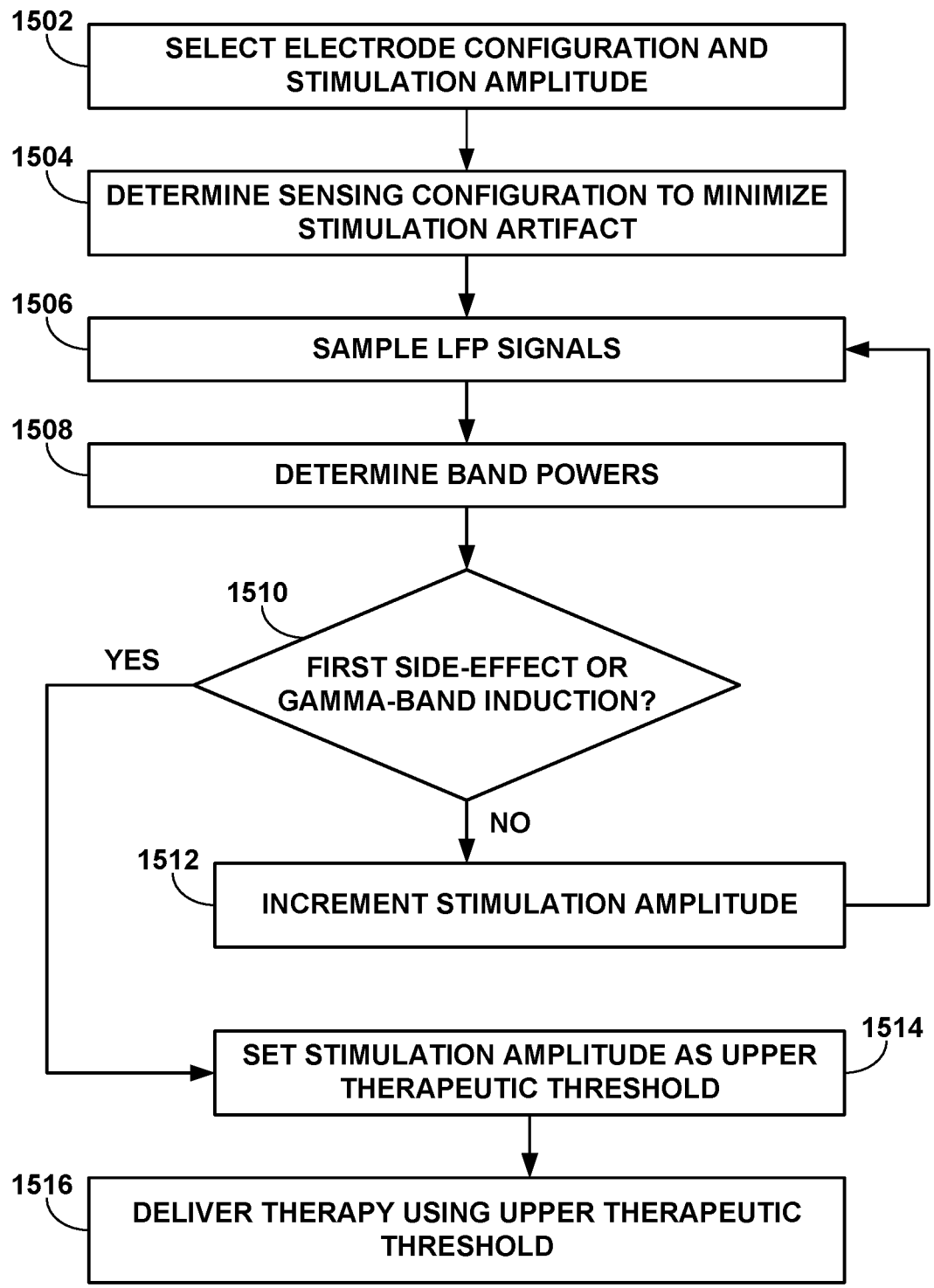
FIG. 15 is a flowchart illustrating an example technique for determining an upper therapeutic threshold for stimulation therapy.

FIG. 15 is a flowchart illustrating an example technique for determining an upper therapeutic threshold for stimulation therapy. The technique of FIG. 15 will be described with respect to processor 210 of IMD 106 in FIG. 2. However, other processors, devices, or combinations thereof, may perform the techniques of FIG. 15 in other examples.

As shown in FIG. 15, processor 210 selects an electrode configuration and an initial stimulation amplitude (1502). Processor 210 then determines the sensing electrode configuration to minimize stimulation artifact (1504) before controlling the delivery of stimulation and sampling of LFP signals (1506). From the LFP signals, processor 210 determines the powers one or more frequency bands (1508). If processor 210 does not determine that there has been a first side-effect due to an increase in the gamma band power ("NO" branch of block 1510), processor 210 increments the stimulation amplitude (1512) and then controls delivery of stimulation with the new stimulation amplitude (1506). Gamma frequency band may be from about 35 Hertz to about 200 Hertz.

If processor 210 determines that there has been a first side-effect due to an increase in the gamma band power ("YES" branch of block 1510), processor 210 sets the current stimulation amplitude as the upper therapeutic threshold (1514). Processor 210 can then control delivery of therapy using the upper therapeutic threshold, such as using an amplitude that is no greater than the upper therapeutic threshold (1516). Processor 210 may repeat the process of FIG. 15 for each electrode combination as part of an electrode sense sweep, and select an electrode combination with the highest upper therapeutic threshold for subsequent stimulation.

Figure 16:
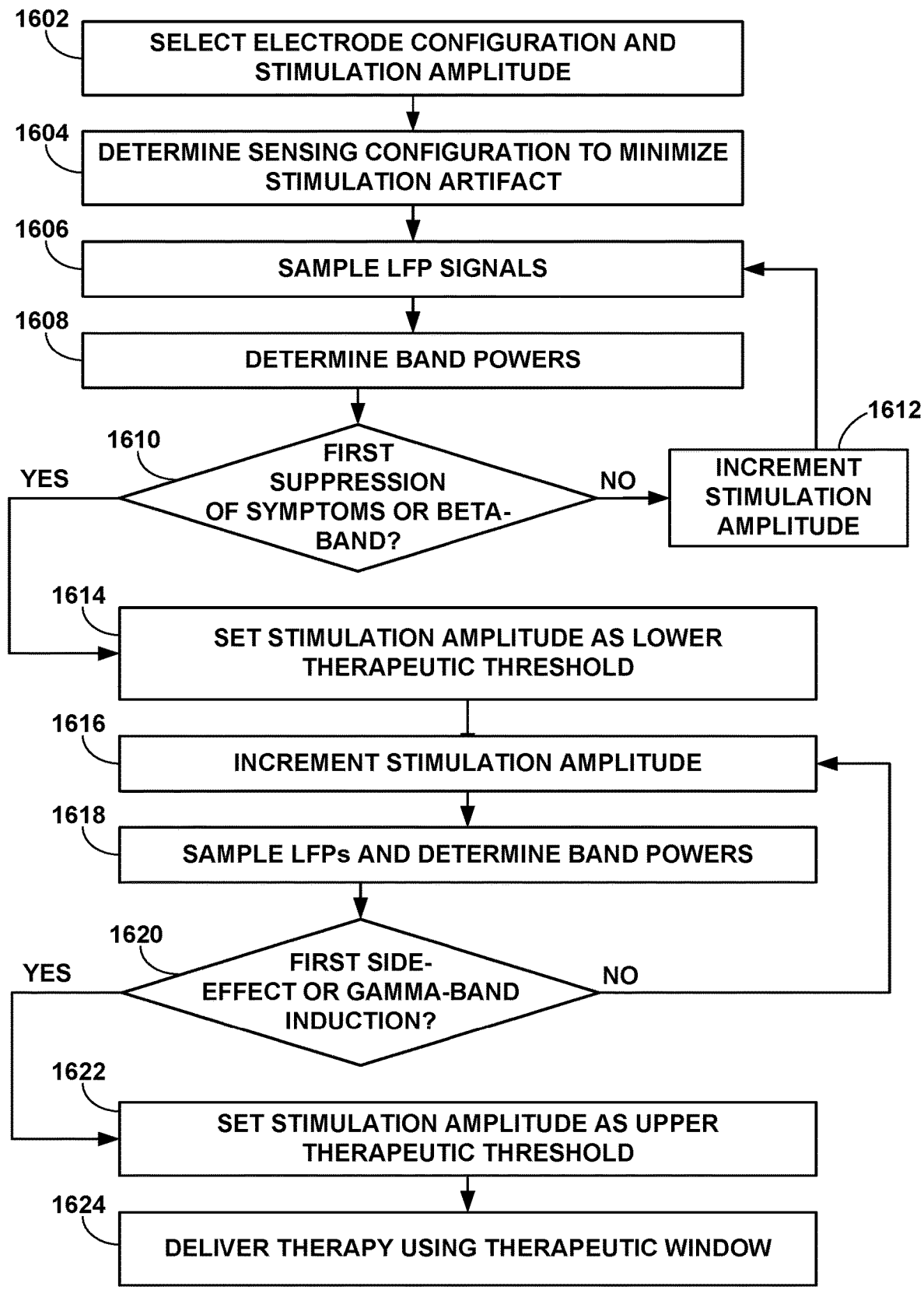
FIG. 16 is a flowchart illustrating an example technique for determining a therapeutic window for stimulation therapy.

FIG. 16 is a flowchart illustrating an example technique for determining a therapeutic window for stimulation therapy, which may be a combination of some processes of FIGS. 16 and 15. The technique of FIG. 16 will be described with respect to processor 210 of IMD 106 in FIG. 2. However, other processors, devices, or combinations thereof, may perform the techniques of FIG. 16 in other examples.

As shown in FIG. 16, processor 210 selects an electrode configuration and an initial stimulation amplitude (1602). Processor 210 then determines the sensing electrode configuration to minimize stimulation artifact (1604) before controlling the delivery of stimulation and sampling of LFP signals (1606). From the LFP signals, processor 210 determines the powers one or more frequency bands (1608). If processor 210 does not determine that there has been a first suppression of symptoms due to a reduction in the beta band power ("NO" branch of block 1610), processor 210 increments the stimulation amplitude (1612) and then controls delivery of stimulation with the new stimulation amplitude (1606). If processor 210 determines that there has been a first suppression of symptoms due to a reduction in the beta band power ("YES" branch of block 1610), processor 210 sets the current stimulation amplitude as the lower therapeutic threshold (1614).

Processor 210 then increments the stimulation amplitude and delivers stimulation again (1616). Processor 210 then samples LFP signals and determines the powers one or more frequency bands (1618). If processor 210 does not determine that there has been a first side-effect due to an increase in the gamma band power ("NO" branch of block 1620), processor 210 increments the stimulation amplitude again (1616). If processor 210 determines that there has been a first side-effect due to an increase in the gamma band power ("YES" branch of block 1620), processor 210 sets the current stimulation amplitude as the upper therapeutic threshold (1622). Processor 210 can then control delivery of therapy using the lower and upper therapeutic thresholds, which may be the therapeutic window, such as using an amplitude that is equal to or between the lower and upper therapeutic thresholds (1624). Processor 210 may repeat the process of FIG. 15 for each electrode combination as part of an electrode sense sweep, and select an electrode combination with the highest upper therapeutic threshold for subsequent stimulation. Alternatively, these sweeps and thresholds may be used to identify lead movement or disease progression, as described herein.

Figure 17:
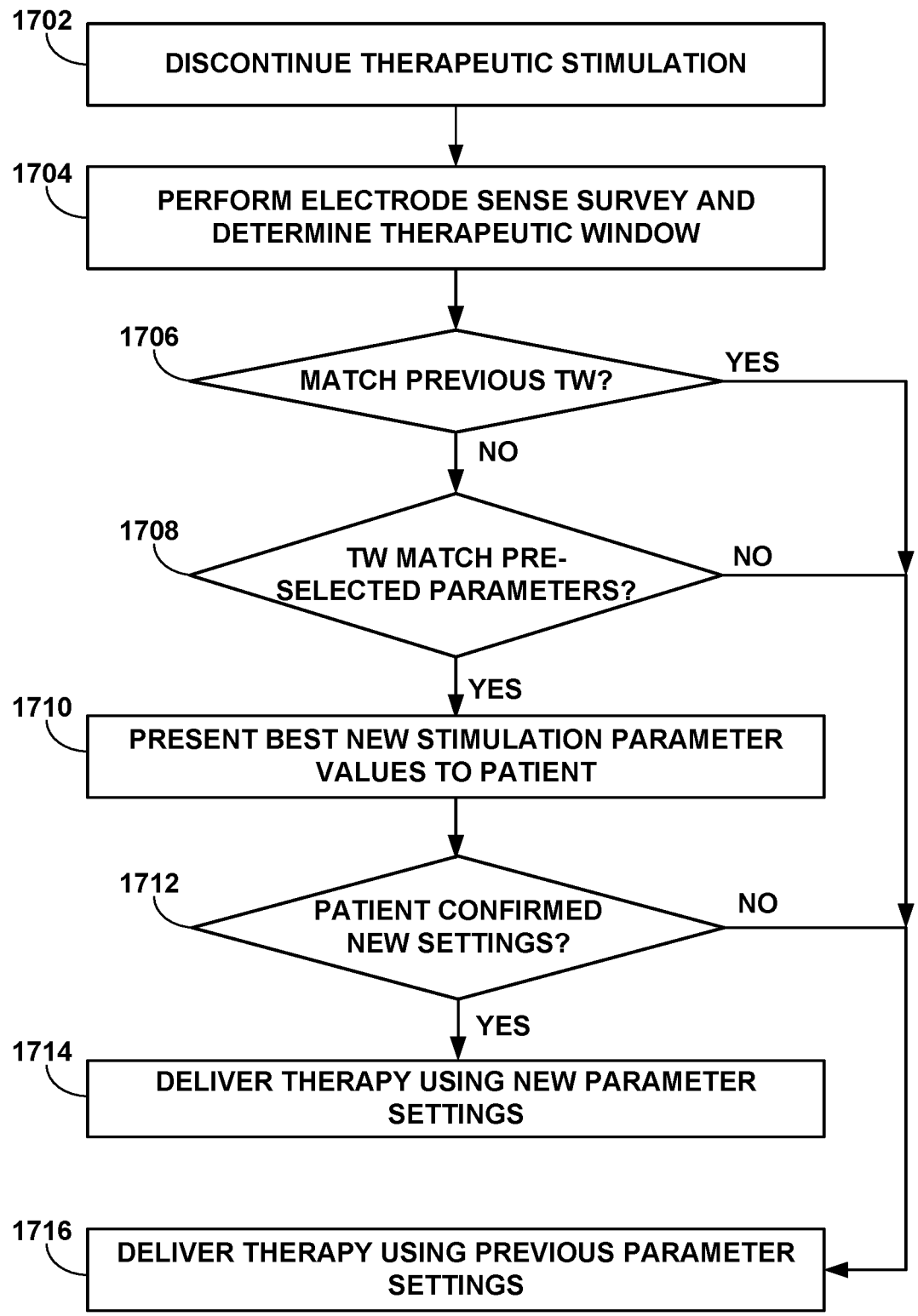
FIG. 17 is a flowchart illustrating an example technique for selecting new parameter values based on therapeutic window determinations for respective electrodes.

FIG. 17 is a flowchart illustrating an example technique for selecting new parameter values based on therapeutic window determinations for respective electrodes. The technique of FIG. 17 will be described with respect to processor 210 of IMD 106 in FIG. 2. However, other processors, devices, or combinations thereof, may perform the techniques of FIG. 17 in other examples.

As shown in FIG. 17, processor 210 discontinues therapeutic stimulation (1702) and then performs the electrode sense survey and determine the therapeutic window (1704) as described herein. If processor 210 determines that the therapeutic window matches the previous therapeutic window ("YES" branch of block 1706), processor 210 continues to deliver therapy using the previous parameter settings (1716). If processor 210 determines that the therapeutic window does not match the previous therapeutic window ("NO" branch of block 1708), processor 210 determines whether values of the new therapeutic window matches pre-selected parameters (1708). If processor 210 determines that the values of the new therapeutic window do not match pre-selected parameters ("NO" branch of block 1708), processor 210 may alert the practitioner of the problem and continue to deliver therapy using previous parameter settings (1716).

If processor 210 determines that the values of the new therapeutic window do match pre-selected parameters ("YES" branch of block 1708), processor 210 may present the best new stimulation parameter values to the patient for confirmation (1710). If processor 210 determines that the patient does not confirm the new settings, such as a time period elapses or the system receives a rejection input from the patient ("NO" branch of block 1712), processor 210 continues to deliver therapy using the previous parameter settings (1716). If processor 210 determines that the patient does confirm the new settings, such receiving a confirmation input from the patient ("YES" branch of block 1712), processor 210 stores the new parameter settings and delivers therapy according to the new parameter settings (1714).

Figure 18:
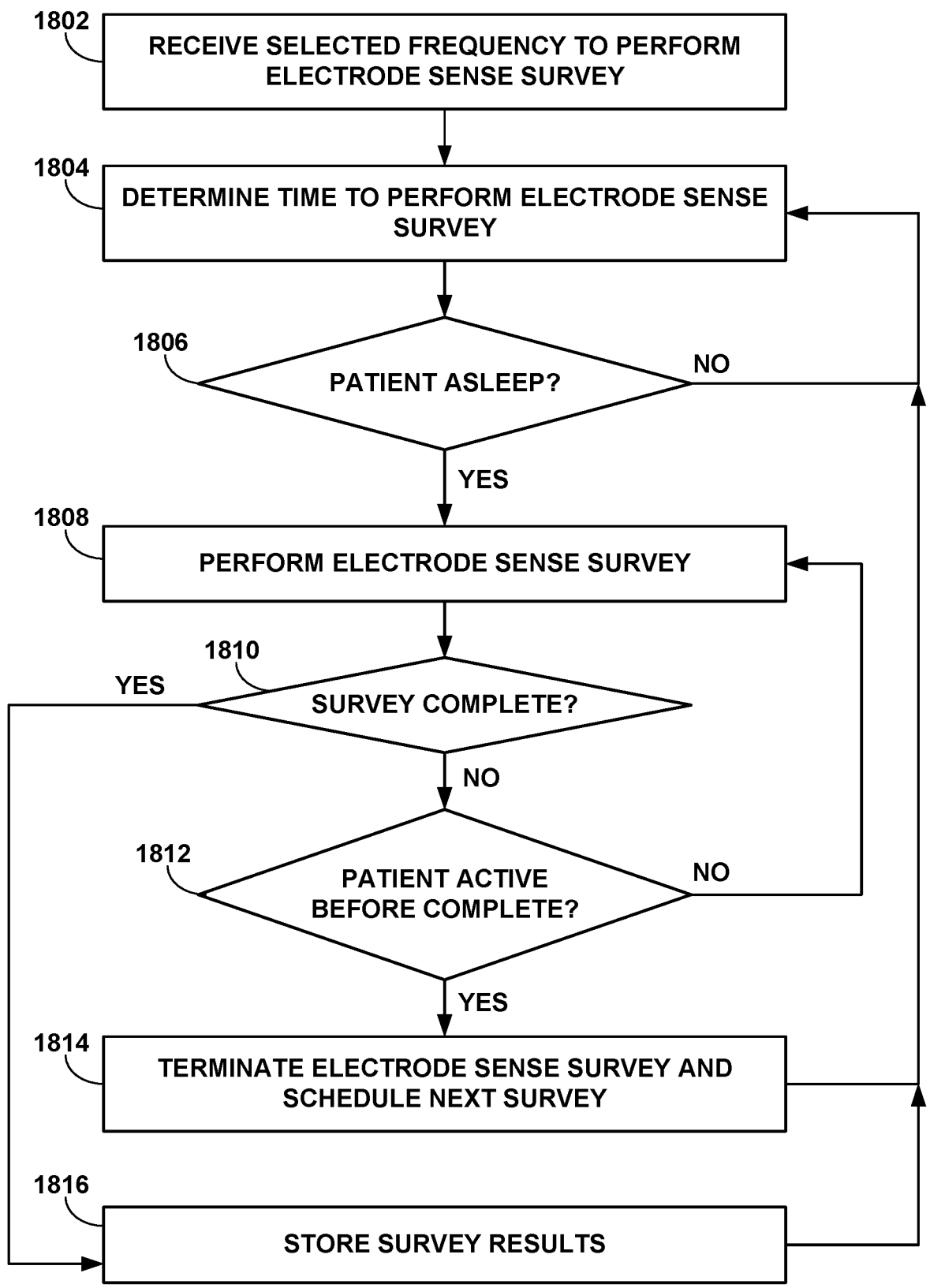
FIG. 18 is a flowchart illustrating an example technique for performing an electrode sense survey.

FIG. 18 is a flowchart illustrating an example technique for performing an electrode sense survey. The technique of FIG. 18 will be described with respect to processor 210 of IMD 106 in FIG. 2. However, other processors, devices, or combinations thereof, may perform the techniques of FIG. 18 in other examples. The electrode sense survey may include determining one or more therapeutic thresholds for some or all electrode combinations of a lead.

In the example of FIG. 18, processor 210 receives a selected frequency to perform the electrode sense survey (1802). Alternatively, processor 210 may automatically initiate the survey in response to a trigger such as improper therapy, system errors, patient or clinician requests, or any other issues. Processor 210 determines the time to perform the electrode sense survey (1804). If processor 210 determines that the patient is not asleep (1806), processor 210 skips the survey. If the patient is asleep, such as to minimize perception of the survey by the patient or reduce patient movement that may affect signal detection, processor 210 performs the electrode sense survey (1808).

If processor 210 determines the survey is complete (1810), processor 210 stores the survey results (1816). Processor also monitors for patient activity before completion (1812). If processor 210 determine that the patient has become active before the survey is complete ("YES" branch of block 1812), processor 210 terminates the electrode sense survey without storing results and schedules the next survey (1814).

Figure 19:
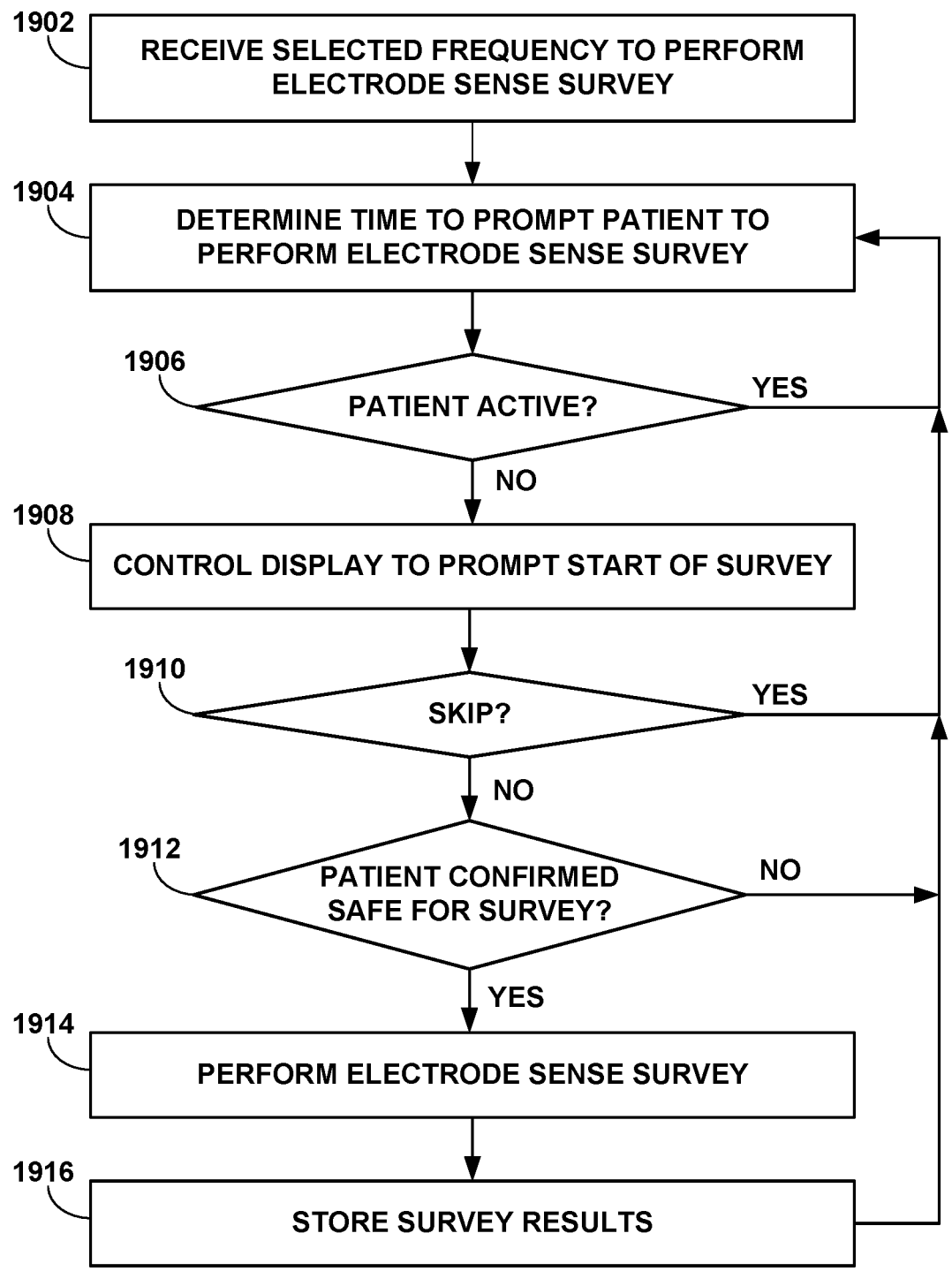
FIG. 19 is a flowchart illustrating an example technique for performing an electrode sense survey.

FIG. 19 is a flowchart illustrating an example technique for performing an electrode sense survey. The technique of FIG. 19 will be described with respect to processor 210 of IMD 106 in FIG. 2. However, other processors, devices, or combinations thereof, may perform the techniques of FIG. 19 in other examples. The electrode sense survey may include determining one or more therapeutic thresholds for some or all electrode combinations of a lead.

In the example of FIG. 19, processor 210 receives a selected frequency to perform the electrode sense survey (1902). Alternatively, processor 210 may automatically initiate the survey in response to a trigger such as improper therapy, system errors, patient or clinician requests, or any other issues. Processor 210 determines the time to prompt the patient perform the electrode sense survey (1904). If processor 210 determines that the patient is active (1906), processor 210 skips the survey. If the patient is not active, such as to reduce patient movement that may affect signal detection, processor 210 controls the display of the programmer to prompt the user to start the electrode sense survey (1908). If processor 210 receives a request to skip the survey ("YES" branch of block 1910), processor 210 determines a new time to perform the survey (1904) the electrode sense survey.

If processor 210 receives confirmation input to start the electrode sense survey ("YES" branch of block 1912), processor 210 performs the electrode sense survey (1914) and stores the survey results (1916). Processor 210 may interrupt and cancel the electrode sense survey before the survey is complete in response to receiving a request to cancel the survey or detecting patient activity that is above a threshold appropriate for the survey.

The following examples are described herein.

EXAMPLE 1

A system includes processing circuitry configured to: receive, for each electrode combination of a plurality of electrode combinations, information representing a signal sensed in response to first electrical stimulation delivered to a patient via a lead, wherein the plurality of electrode combinations comprises different electrode combinations comprising electrode disposed at different positions around a perimeter of the lead implanted in the patient; determine, based on the information for each electrode combination of the plurality of electrode combinations, values for a threshold at different locations around the perimeter of the lead; and determine, based on the values for the threshold, one or more stimulation parameter values that at least partially define second electrical stimulation deliverable to the patient via the lead.

EXAMPLE 2

The system of example 1, wherein the one or more stimulation parameter values comprises an electrode combination.

EXAMPLE 3

The system of any of examples 1 and 2, wherein the processing circuitry is configured to control stimulation generation circuitry of a medical device to deliver the first electrical stimulation and control the stimulation generation circuitry to deliver the second electrical stimulation as stimulation therapy.

EXAMPLE 4

The system of any of examples 1 through 3, wherein the threshold comprises a lower therapeutic threshold, and wherein the values for the lower therapeutic threshold indicate stimulation parameter values below which electrical stimulation does not induce a therapeutic benefit in the patient at the respective different locations.

EXAMPLE 5

The system of any of examples 1 through 4, wherein the threshold comprises an upper therapeutic threshold, and wherein the values for the upper therapeutic threshold indicate stimulation parameter values above which electrical stimulation induces a side-effect in the patient at the respective different locations.

EXAMPLE 6

The system of any of examples 1 through 5, wherein the information representing the signal sensed comprises first information representing a first signal sensed, wherein the threshold comprises a lower therapeutic threshold and the values for the threshold comprise first values for the lower therapeutic threshold, wherein the first values for the lower therapeutic threshold indicate stimulation parameter values below which electrical stimulation does not induce a therapeutic benefit in the patient at the respective different locations, and wherein the processing circuitry is further configured to: receive, for each electrode combination of the plurality of electrode combinations, second information representing a second signal sensed in response to third electrical stimulation delivered to the patient via the lead; determine, based on the second information for each electrode combination of the plurality of electrode combinations, second values for an upper therapeutic threshold at the different locations around the perimeter of the lead; and determine, based on the first values for the lower therapeutic threshold and the second values for the upper therapeutic threshold, one or more stimulation parameter values that at least partially define the second electrical stimulation deliverable to the patient via the lead.

EXAMPLE 7A

The system of example 6, wherein the first signal and the second signal comprises local field potentials (LFPs), and wherein the processing circuitry is configured to: determine the first values for the lower therapeutic threshold based on a characteristic within a Beta band of the LFPs of the first signal; and determine the second values for the upper therapeutic threshold based on a characteristic within a Gamma band of the LFPs of the second signal.

EXAMPLE 7B

The system of example 6, wherein the first signal and the second signal comprises evoked signals, and wherein the processing circuitry is configured to: determine the first values for the lower therapeutic threshold based on a characteristic of at least a first evoked signal of the first signal; and determine the second values for the upper therapeutic threshold based on a characteristic of at least a second evoked signal of the second signal.

EXAMPLE 8

The system of any of examples 6 and 7, wherein the processing circuitry is configured to: receive first feedback representative of first patient input indicating suppression of symptoms caused by the first electrical stimulation; determine the first values for the lower therapeutic threshold based on the first feedback representative of the first patient input; receive second feedback representative of patient input indicating a side-effect of the third electrical stimulation; and determine the second values for the upper therapeutic threshold based on the second feedback representative of the second patient input.

EXAMPLE 9

The system of any of examples 6 through 8, wherein the processing circuitry is further configured to: determine therapeutic window metrics based on a difference between the first values for the lower therapeutic threshold and the second values for the upper therapeutic threshold at respective different locations around the perimeter of the lead; and determine the one or more stimulation parameter values by at least determining an electrode combination corresponding to a location of the different locations corresponding to a largest therapeutic window metric of the therapeutic window metrics, wherein the electrode combination at least partially defines the second electrical stimulation deliverable to the patient via the lead.

EXAMPLE 10

The system of any of examples 1 through 9, wherein the information representing the signal sensed comprises first information representing a first signal sensed at a first time, wherein the values for the threshold comprise first values for the threshold, and wherein the processing circuitry is configured to: receive, for each electrode combination of the plurality of electrode combinations, second information representing a second signal sensed at a second time and in response to third electrical stimulation delivered to the patient via the lead; determine, based on the second information, second values for the threshold at the different locations around the perimeter of the lead; compare the first values for the threshold to the second values for the threshold at the respective different locations; and determine, based on the comparison, a change to an electrode combination, the one or more stimulation parameter values comprising the electrode combination.

EXAMPLE 11

The system of any of examples 1 through 10, wherein the information representing the signal sensed comprises first information representing a first signal sensed at a first time, wherein the values for the threshold comprise first values for the threshold, and wherein the processing circuitry is configured to: receive, for each electrode combination of the plurality of electrode combinations, second information representing a second signal sensed at a second time and in response to third electrical stimulation delivered to the patient via the lead; determine, based on the second information, second values for the threshold at the different locations around the perimeter of the lead; compare the first values for the threshold to the second values for the threshold at the respective different locations; and determine, based on the comparison, a change to a severity of a condition of the patient.

EXAMPLE 12

The system of any of examples 1 through 11, further comprising an implantable medical device, wherein the implantable medical device comprises the processing circuitry.

EXAMPLE 13

A method includes receiving, by processing circuitry and for each electrode combination of a plurality of electrode combinations, information representing a signal sensed in response to first electrical stimulation delivered to a patient via a lead, wherein the plurality of electrode combinations comprise different electrode combinations comprising electrode disposed at different positions around a perimeter of the lead implanted in the patient; determining, by the processing circuitry and based on the information for each electrode combination of the plurality of electrode combinations, values for a threshold at different locations around the perimeter of the lead; and determining, by the processing circuitry and based on the values for the threshold, one or more stimulation parameter values that at least partially define second electrical stimulation deliverable to the patient via the lead.

EXAMPLE 14

The method of example 13, wherein the one or more stimulation parameter values comprises an electrode combination.

EXAMPLE 14

The method of any of examples 13 and 14, further comprising controlling, by the processing circuitry, stimulation generation circuitry of a medical device to deliver the first electrical stimulation and control the stimulation generation circuitry to deliver the second electrical stimulation as stimulation therapy.

EXAMPLE 15

The method of any of examples 13 through 15, wherein the threshold comprises a lower therapeutic threshold, and wherein the values for the lower therapeutic threshold indicate stimulation parameter values below which electrical stimulation does not induce a therapeutic benefit in the patient at the respective different locations.

EXAMPLE 16

The method of any of examples 13 through 16, wherein the threshold comprises an upper therapeutic threshold, and wherein the values for the upper therapeutic threshold indicate stimulation parameter values above which electrical stimulation induces a side-effect in the patient at the respective different locations.

EXAMPLE 17

The method of any of examples 13 through 17, wherein the information representing the signal sensed comprises first information representing a first signal sensed, wherein the threshold comprises a lower therapeutic threshold and the values for the threshold comprise first values for the lower therapeutic threshold, wherein the first values for the lower therapeutic threshold indicate stimulation parameter values below which electrical stimulation does not induce a therapeutic benefit in the patient at the respective different locations, and wherein the method further comprises: receiving, for each electrode combination of the plurality of electrode combinations, second information representing a second signal sensed in response to third electrical stimulation delivered to the patient via the lead; determining, based on the second information for each electrode combination of the plurality of electrode combinations, second values for an upper therapeutic threshold at the different locations around the perimeter of the lead; and determining, based on the first values for the lower therapeutic threshold and the second values for the upper therapeutic threshold, one or more stimulation parameter values that at least partially define the second electrical stimulation deliverable to the patient via the lead.

EXAMPLE 18

The method of any of examples 17 and 18, wherein the first signal and the second signal comprises local field potentials (LFPs), and wherein the method further comprises: determining the first values for the lower therapeutic threshold based on a characteristic within a Beta band of the LFPs of the first signal; and determining the second values for the upper therapeutic threshold based on a characteristic within a Gamma band of the LFPs of the second signal.

EXAMPLE 19

The method of any of examples 17 through 19, further includes receiving first feedback representative of first patient input indicating suppression of symptoms caused by the first electrical stimulation; determining the first values for the lower therapeutic threshold based on the first feedback representative of the first patient input; receiving second feedback representative of patient input indicating a side-effect of the third electrical stimulation; and determining the second values for the upper therapeutic threshold based on the second feedback representative of the second patient input.

EXAMPLE 20

The method of any of examples 17 through 20, further includes determining therapeutic window metrics based on a difference between the first values for the lower therapeutic threshold and the second values for the upper therapeutic threshold at respective different locations around the perimeter of the lead; and determining the one or more stimulation parameter values by at least determining an electrode combination corresponding to a location of the different locations corresponding to a largest therapeutic window metric of the therapeutic window metrics, wherein the electrode combination at least partially defines the second electrical stimulation deliverable to the patient via the lead.

EXAMPLE 21

The method of any of examples 13 through 21, wherein the information representing the signal sensed comprises first information representing a first signal sensed at a first time, wherein the values for the threshold comprise first values for the threshold, and wherein the method further comprises: receiving, for each electrode combination of the plurality of electrode combinations, second information representing a second signal sensed at a second time and in response to third electrical stimulation delivered to the patient via the lead; determining, based on the second information, second values for the threshold at the different locations around the perimeter of the lead; comparing the first values for the threshold to the second values for the threshold at the respective different locations; and determining, based on the comparison, a change to an electrode combination, the one or more stimulation parameter values comprising the electrode combination.

EXAMPLE 22

The method of any of examples 13 through 22, wherein the information representing the signal sensed comprises first information representing a first signal sensed at a first time, wherein the values for the threshold comprise first values for the threshold, and wherein the method further comprises: receiving, for each electrode combination of the plurality of electrode combinations, second information representing a second signal sensed at a second time and in response to third electrical stimulation delivered to the patient via the lead; determining, based on the second information, second values for the threshold at the different locations around the perimeter of the lead; comparing the first values for the threshold to the second values for the threshold at the respective different locations; and determining, based on the comparison, a change to a severity of a condition of the patient.

EXAMPLE 23

A computer-readable storage medium comprising instructions that, when executed, cause processing circuitry to receive, for each electrode combination of a plurality of electrode combinations, information representing a signal sensed in response to first electrical stimulation delivered to a patient via a lead, wherein the plurality of electrode combinations comprise different electrode combinations comprising electrode disposed at different positions around a perimeter of the lead implanted in the patient; determine, based on the information for each electrode combination of the plurality of electrode combinations, values for a threshold at different locations around the perimeter of the lead; and determine, based on the values for the threshold, one or more stimulation parameter values that at least partially define second electrical stimulation deliverable to the patient via the lead.

The techniques described in this disclosure may be implemented, at least in part, in hardware, software, firmware or any combination thereof. For example, various aspects of the described techniques may be implemented within one or more processors, such as fixed function processing circuitry and/or programmable processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit comprising hardware may also perform one or more of the techniques of this disclosure.

Such hardware, software, and firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

The techniques described in this disclosure may also be embodied or encoded in a computer-readable medium, such as a computer-readable storage medium, containing instructions. Instructions embedded or encoded in a computer-readable storage medium may cause a programmable processor, or other processor, to perform the method, e.g., when the instructions are executed. Computer readable storage media may include random access memory (RAM), ferroelectric random access memory (FRAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

Various examples have been described. These and other examples are within the scope of the following claims.

What is claimed is:

1. A system comprising:
processing circuitry configured to:
receive, for each respective electrode combination of a plurality of electrode combinations, information representing a signal sensed in response to first electrical stimulation delivered to a patient via the respective electrode combination of a lead, wherein the plurality of electrode combinations comprises different electrode combinations comprising at least one electrode disposed at different positions around a perimeter of the lead implanted in the patient;
determine, based on the information for each respective electrode combination of the plurality of electrode combinations, values for a lower threshold and an upper threshold at different locations around the perimeter of the lead; and
determine, based on the values for the lower threshold and the upper threshold, one or more stimulation parameter values that at least partially define second electrical stimulation deliverable to the patient via the lead.

2. The system of claim 1, wherein the one or more stimulation parameter values comprises an electrode combination.

3. The system of claim 1, wherein the processing circuitry is configured to control stimulation generation circuitry of a medical device to deliver the first electrical stimulation and control the stimulation generation circuitry to deliver the second electrical stimulation as stimulation therapy.

4. The system of claim 1, wherein the lower threshold comprises a lower therapeutic threshold, and wherein the values for the lower therapeutic threshold indicate stimulation parameter values below which electrical stimulation does not induce a therapeutic benefit in the patient at the respective different locations.

5. The system of claim 1, wherein the upper threshold comprises an upper therapeutic threshold, and wherein the values for the upper therapeutic threshold indicate stimulation parameter values above which electrical stimulation induces a side-effect in the patient at the respective different locations.

6. The system of claim 1, wherein the information representing the signal sensed comprises first information representing a first signal sensed, wherein the lower threshold comprises a lower therapeutic threshold and the values for the lower threshold comprise first values for the lower therapeutic threshold, wherein the first values for the lower therapeutic threshold indicate stimulation parameter values below which electrical stimulation does not induce a therapeutic benefit in the patient at the respective different locations, and wherein the processing circuitry is further configured to:
receive, for each electrode combination of the plurality of electrode combinations, second information representing a second signal sensed in response to third electrical stimulation delivered to the patient via the lead;
determine, based on the second information for each electrode combination of the plurality of electrode combinations, second values for an upper therapeutic threshold at the different locations around the perimeter of the lead; and
determine, based on the first values for the lower therapeutic threshold and the second values for the upper therapeutic threshold, one or more stimulation parameter values that at least partially define the second electrical stimulation deliverable to the patient via the lead.

7. The system of claim 6, wherein the first signal and the second signal comprises local field potentials (LFPs), and wherein the processing circuitry is configured to:
determine the first values for the lower therapeutic threshold based on a characteristic within a Beta band of the LFPs of the first signal; and
determine the second values for the upper therapeutic threshold based on a characteristic within a Gamma band of the LFPs of the second signal.

8. The system of claim 6, wherein the first signal and the second signal comprises evoked signals, and wherein the processing circuitry is configured to:
determine the first values for the lower therapeutic threshold based on a characteristic of at least a first evoked signal of the first signal; and
determine the second values for the upper therapeutic threshold based on a characteristic of at least a second evoked signal of the second signal.

9. The system of claim 6, wherein the processing circuitry is configured to:
receive first feedback representative of first patient input indicating suppression of symptoms caused by the first electrical stimulation;
determine the first values for the lower therapeutic threshold based on the first feedback representative of the first patient input;
receive second feedback representative of patient input indicating a side-effect of the third electrical stimulation; and
determine the second values for the upper therapeutic threshold based on the second feedback representative of the second patient input.

10. The system of claim 6, wherein the processing circuitry is further configured to:
- determine therapeutic window metrics based on a difference between the first values for the lower therapeutic threshold and the second values for the upper therapeutic threshold at respective different locations around the perimeter of the lead; and
- determine the one or more stimulation parameter values by at least determining an electrode combination corresponding to a location of the different locations corresponding to a largest therapeutic window metric of the therapeutic window metrics, wherein the electrode combination at least partially defines the second electrical stimulation deliverable to the patient via the lead.

11. The system of claim 1, wherein the information representing the signal sensed comprises first information representing a first signal sensed at a first time, wherein the values for the lower threshold and the upper threshold comprise first values for the lower threshold and the upper threshold, and wherein the processing circuitry is configured to:
- receive, for each electrode combination of the plurality of electrode combinations, second information representing a second signal sensed at a second time and in response to third electrical stimulation delivered to the patient via the lead;
- determine, based on the second information, second values for the lower threshold and the upper threshold at the different locations around the perimeter of the lead;
- compare the first values for the threshold to the second values for the lower threshold and the upper threshold at the respective different locations; and
- determine, based on the comparison, a change to an electrode combination, the one or more stimulation parameter values comprising the electrode combination.

12. The system of claim 1, wherein the information representing the signal sensed comprises first information representing a first signal sensed at a first time, wherein the values for the lower threshold and the upper threshold comprise first values for the lower threshold and the upper threshold, and wherein the processing circuitry is configured to:
- receive, for each electrode combination of the plurality of electrode combinations, second information representing a second signal sensed at a second time and in response to third electrical stimulation delivered to the patient via the lead;
- determine, based on the second information, second values for the lower threshold and the upper threshold at the different locations around the perimeter of the lead;
- compare the first values for the lower threshold and the upper threshold to the second values for the lower threshold and the upper threshold at the respective different locations; and
- determine, based on the comparison, a change to a severity of a condition of the patient.

13. The system of claim 1, further comprising an implantable medical device, wherein the implantable medical device comprises the processing circuitry.

14. A method comprising:
- receiving, by processing circuitry and for each respective electrode combination of a plurality of electrode combinations, information representing a signal sensed in response to first electrical stimulation delivered to a patient via the respective electrode combination of a lead, wherein the plurality of electrode combinations comprise different electrode combinations comprising at least one electrode disposed at different positions around a perimeter of the lead implanted in the patient;
- determining, by the processing circuitry and based on the information for each respective electrode combination of the plurality of electrode combinations, values for a lower threshold and an upper threshold at different locations around the perimeter of the lead; and
- determining, by the processing circuitry and based on the values for the lower threshold and the upper threshold, one or more stimulation parameter values that at least partially define second electrical stimulation deliverable to the patient via the lead.

15. The method of claim 14, wherein the one or more stimulation parameter values comprises an electrode combination.

16. The method of claim 14, further comprising controlling, by the processing circuitry, stimulation generation circuitry of a medical device to deliver the first electrical stimulation and control the stimulation generation circuitry to deliver the second electrical stimulation as stimulation therapy.

17. The method of claim 14, wherein the lower threshold comprises a lower therapeutic threshold, and wherein the values for the lower therapeutic threshold indicate stimulation parameter values below which electrical stimulation does not induce a therapeutic benefit in the patient at the respective different locations.

18. The method of claim 14, wherein the upper threshold comprises an upper therapeutic threshold, and wherein the values for the upper therapeutic threshold indicate stimulation parameter values above which electrical stimulation induces a side-effect in the patient at the respective different locations.

19. The method of claim 14, wherein the information representing the signal sensed comprises first information representing a first signal sensed, wherein the lower threshold comprises a lower therapeutic threshold and the values for the lower threshold comprise first values for the lower therapeutic threshold, wherein the first values for the lower therapeutic threshold indicate stimulation parameter values below which electrical stimulation does not induce a therapeutic benefit in the patient at the respective different locations, and wherein the method further comprises:
- receiving, for each electrode combination of the plurality of electrode combinations, second information representing a second signal sensed in response to third electrical stimulation delivered to the patient via the lead;
- determining, based on the second information for each electrode combination of the plurality of electrode combinations, second values for an upper therapeutic threshold at the different locations around the perimeter of the lead; and
- determining, based on the first values for the lower therapeutic threshold and the second values for the upper therapeutic threshold, one or more stimulation parameter values that at least partially define the second electrical stimulation deliverable to the patient via the lead.

20. The method of claim 19, wherein the first signal and the second signal comprises local field potentials (LFPs), and wherein the method further comprises:
- determining the first values for the lower therapeutic threshold based on a characteristic within a Beta band of the LFPs of the first signal; and determining the second values for the upper therapeutic threshold based on a characteristic within a Gamma band of the LFPs of the second signal.

21. The method of claim 19, further comprising:

receiving first feedback representative of first patient input indicating suppression of symptoms caused by the first electrical stimulation;

determining the first values for the lower therapeutic threshold based on the first feedback representative of the first patient input;

receiving second feedback representative of patient input indicating a side-effect of the third electrical stimulation; and determining the second values for the upper therapeutic threshold based on the second feedback representative of the second patient input.

22. The method of claim 19, further comprising:

determining therapeutic window metrics based on a difference between the first values for the lower therapeutic threshold and the second values for the upper therapeutic threshold at respective different locations around the perimeter of the lead; and determining the one or more stimulation parameter values by at least determining an electrode combination corresponding to a location of the different locations corresponding to a largest therapeutic window metric of the therapeutic window metrics, wherein the electrode combination at least partially defines the second electrical stimulation deliverable to the patient via the lead.

23. The method of claim 14, wherein the information representing the signal sensed comprises first information representing a first signal sensed at a first time, wherein the values for the lower threshold and the upper threshold comprise first values for the lower threshold and the upper threshold, and wherein the method further comprises:

receiving, for each electrode combination of the plurality of electrode combinations, second information representing a second signal sensed at a second time and in response to third electrical stimulation delivered to the patient via the lead;

determining, based on the second information, second values for the lower threshold and the upper threshold at the different locations around the perimeter of the lead;

comparing the first values for the lower threshold and the upper threshold to the second values for the lower threshold and the upper threshold at the respective different locations; and determining, based on the comparison, a change to an electrode combination, the one or more stimulation parameter values comprising the electrode combination.

24. The method of claim 14, wherein the information representing the signal sensed comprises first information representing a first signal sensed at a first time, wherein the values for the lower threshold and the upper threshold comprise first values for the lower threshold and the upper threshold, and wherein the method further comprises:

receiving, for each electrode combination of the plurality of electrode combinations, second information representing a second signal sensed at a second time and in response to third electrical stimulation delivered to the patient via the lead;

determining, based on the second information, second values for the lower threshold and the upper threshold at the different locations around the perimeter of the lead;

comparing the first values for the lower threshold and the upper threshold to the second values for the lower threshold and the upper threshold at the respective different locations; and determining, based on the comparison, a change to a severity of a condition of the patient.

25. A computer-readable storage medium comprising instructions that, when executed, cause processing circuitry to:

receive, for each respective electrode combination of a plurality of electrode combinations, information representing a signal sensed in response to first electrical stimulation delivered to a patient via the respective electrode combination of a lead, wherein the plurality of electrode combinations comprise different electrode combinations comprising at least one electrode disposed at different positions around a perimeter of the lead implanted in the patient;

determine, based on the information for each respective electrode combination of the plurality of electrode combinations, values for a lower threshold and an upper threshold at different locations around the perimeter of the lead; and determine, based on the values for the lower threshold and the upper threshold, one or more stimulation parameter values that at least partially define second electrical stimulation deliverable to the patient via the lead.

\* \* \* \* \*